United States Patent [19]
O'Malley et al.

[11] Patent Number: 5,925,766
[45] Date of Patent: Jul. 20, 1999

[54] SUBSTITUTED 3-(AMINOALKYLAMINO)-1, 2-BENZISOXAZOLES AND RELATED COMPOUNDS

[75] Inventors: Gerard J. O'Malley, Newtown, Pa.; Mark G. Palermo, Netcong, N.J.

[73] Assignee: Hoechst Marion Roussel, Inc., Cincinnati, Ohio

[21] Appl. No.: 08/816,817

[22] Filed: Mar. 18, 1997

Related U.S. Application Data

[60] Continuation of application No. 08/470,393, Jun. 6, 1995, abandoned, which is a division of application No. 08/150,301, Nov. 12, 1993, Pat. No. 5,494,908, which is a continuation-in-part of application No. 07/980,021, Nov. 23, 1992, abandoned.

[51] Int. Cl.⁶ ................. C07D 261/20; C07D 275/04; C07D 231/56
[52] U.S. Cl. ............... 548/212; 548/241; 548/362.5
[58] Field of Search .................... 548/212, 241, 548/362.5

[56] References Cited

U.S. PATENT DOCUMENTS

| | | | |
|---|---|---|---|
| 3,681,382 | 8/1972 | Gschwend | 548/362.1 |
| 3,707,364 | 12/1972 | Becke et al. | 71/90 |
| 3,725,431 | 4/1973 | Gschwend | 260/310 |
| 4,533,731 | 8/1985 | Ibuki et al. | 544/140 |
| 4,844,728 | 7/1989 | Yamamoto et al. | 71/92 |
| 5,494,908 | 2/1996 | O'Malley et al. | 514/228.2 |
| 5,580,982 | 12/1996 | O'Malley et al. | 546/198 |

OTHER PUBLICATIONS

Zani et al., Il Farmaco, 44(10), 997–1006, 1989.

*Primary Examiner*—Fiona T. Powers
*Attorney, Agent, or Firm*—Michael J. Sayles

[57] ABSTRACT

This application relates to compounds of the formula

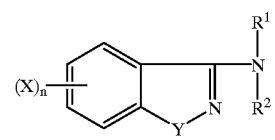

wherein $R^1$, X, Y and n are as defined in the specification; and pharmaceutically acceptable addition salts thereof and optical and geometric isomers or racemic mixtures thereof; which compounds are useful or the treatment of various memory dysfunctions characterized by a decreased cholinergic function such as Alzheimer's disease. Compounds of this invention also inhibit monoamine oxidase and hence are useful as antidepressants.

5 Claims, No Drawings

SUBSTITUTED 3-(AMINOALKYLAMINO)-1, 2-BENZISOXAZOLES AND RELATED COMPOUNDS

This is a continuation of application Ser. No. 08/470,393, filed Jun. 6, 1995, now abandoned, which is a divisional of Ser. No. 08/150,301, filed Nov. 12, 1993, now U.S. Pat. No. 5,494,908; which is a continuation-in-part of Ser. No. 07/980,021, filed Nov. 23, 1992, now abandoned.

This application is a continuation-in-part application of pending U.S. patent application Ser. No. 980,021, filed Nov. 23, 1992.

This application relates to compounds of the formula

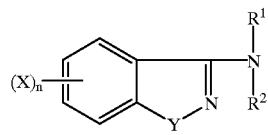

wherein
$R^1$ is hydrogen, $(C_1-C_6)$alkyl, aryl$(C_1-C_6)$alkyl, $(C_1-C_6)$alkoxycarbonyl, aryloxycarbonyl, aryl$(C_1-C_6)$alkoxycarbonyl, aminocarbonyl, $(C_1-C_6)$alkylaminocarbonyl, or di$(C_1-C_6)$alkylaminocarbonyl, X is hydrogen, $(C_1-C_6)$alkyl, $(C_1-C_6)$alkoxy, $(C_1-C_6)$alkoxymethyleneoxy, aryl$(C_1-C_6)$alkoxy, halo, hydroxy, amino, $(C_1-C_6)$alkylamino, di$(C_1-C_6)$alkylamino, aryl$(C_1-C_6)$alkylamino, $(C_1-C_6)$alkanoylamino, aminocarbonyloxy, $(C_1-C_{10})$alkylaminocarbonyloxy, di$(C_1-C_{10})$alkylaminocarbonyloxy, tetrahydroisoquinolylcarbonyloxyl, aryl$(C_1-C_{10})$alkylaminocarbonyloxy, $(C_1-C_6)$alkoxycarbonyloxy, aryl $(C_1-C_6)$alkylcarbonyloxy;

Y is oxygen (O), sulfur (S) or $NR^{10}$ where $R^{10}$ is hydrogen, $(C_1-C_6)$alkyl, aryl or aryl$(C_1-C_6)$alkyl;

$R^2$ is

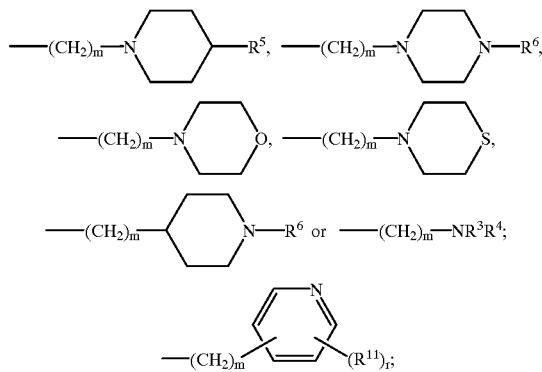

or $R^1$ and $R^2$ together with the nitrogen to which they are attached form the ring

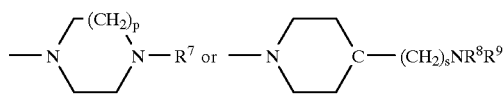

where
$R^3$ is hydrogen, $(C_1-C_6)$alkyl, aryl$(C_1-C_6)$alkyl, $(C_1-C_6)$alkylcarbonyl, $(C_1-C_6)$alkoxycarbonyl, $(C_3-C_6)$alkenyl, $(C_3-C_6)$alkynyl, aryl, amino$(C_1-C_6)$alkyl, mono$(C_1-C_6)$alkylamino$(C_1-C_6)$alkyl or di$(C_1-C_6)$alkylamino$(C_1-C_6)$alkyl;

$R^4$ is hydrogen or $(C_1-C_6)$alkyl;
$R^5$ is hydrogen, hydroxy, $(C_1-C_6)$alkoxy, amino $(C_1-C_6)$alkyl, monoaryl$(C_1-C_6)$alkylamino$(C_1-C_6)$alkyl, diaryl$(C_1-C_6)$alkylamino$(C_1-C_6)$alkyl, $(C_1 14\ C_6)$alkylamino$(C_1-C_6)$alkyl, $(C_1-C_6)$alkanoyloxy or aryl$(C_1-C_6)$alkyl;
$R^6$ is hydrogen, $(C_1-C_6)$alkyl, aryl, aryl$(C_1-C_6)$alkyl, $(C_1-C_6)$alkylcarbonyl, aryl$(C_1-C_6)$alkylcarbonyl or $(C_1-C_6)$alkoxycarbonyl;
$R^7$ is hydrogen, $(C_1-C_6)$alkyl, $(C_2-C_6)$alkenyl, $(C_3-C_6)$alkynyl, phenyl, aryl$(C_1-C_6)$alkyl, pyridyl, pyrimidyl, pyridazinyl, pyrazinyl or quinolinyl;
$R^8$ and $R^9$ are independently hydrogen, $(C_1-C_6)$alkyl or aryl$(C_1-C_6)$alkyl;
$R^{11}$ is $(C_1-C_6)$alkyl, $(C_1-C_6)$alkoxy, hydroxy, halogen, nitro or trifluoromethyl;
m is an integer from 2 to 7;
n is an integer from 0 to 3;
p is an integer from 1 to 3;
r is an integer from 0 to 2; and
s is an integer from 0 to 6;

and pharmaceutically acceptable addition salts thereof and optical and geometric isomers or racemic mixtures thereof; which compounds are useful for the treatment of various memory dysfunctions characterized by a decreased cholinergic function such as Alzheimer's disease. Compounds of this invention also inhibit monoamine oxidase and hence are useful as antidepressants.

Unless otherwise stated or indicated, the following definitions shall apply through the specification and the appended claims.

The term $(C_1-C_6)$alkyl or $(C_1-C_{10})$alkyl shall means a straight or branched alkyl group, for example, methyl, ethyl, n-propyl, isopropyl, n-butyl, iso-butyl, sec-butyl, t-butyl and straight and branched chain pentyl, hexyl, heptyl and decyl.

The term halo shall mean fluorine, chlorine, bromine or iodine.

The terms phenyl pyrimidyl, pyridazinyl, pyrazinyl and quinolinyl shall mean the respective group substituted with 0, 1 or 2 substituents each of which being independently $(C_1-C_6)$alkyl, $(C_1-C_6)$alkoxy, hydroxy, halogen, nitro or trifluoromethyl.

The term pyridyl shall mean a 2-pyridyl, 3-pyridyl or 4-pyridyl group substituted with 0, 1 or 2 substituents each of which being independently $(C_1-C_6)$alkyl, $(C_1-C_6)$alkoxy, hydroxy, halogen, nitro or trifluoromethyl.

Throughout the specification and the appended claims, a given chemical formula or name shall encompass all stereo, optical, enantiomeric and tautomeric isomers where such isomers exists.

In one class of compounds of this invention are compounds of the formula

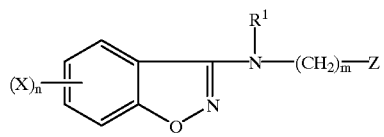

wherein X, $R^1$, n and m are as defined above and Z is

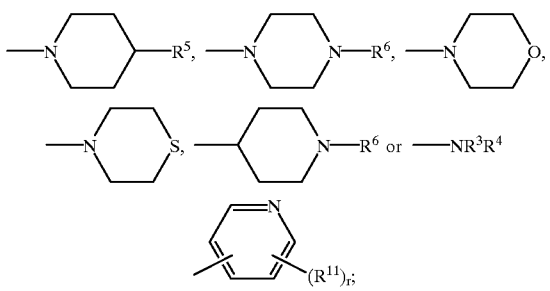

$R^3$ is hydrogen, $(C_1-C_6)$alkyl, aryl$(C_1-C_6)$alkyl, $(C_1-C_6)$ alkoxycarbonyl, $(C_1-C_6)$alkoxycarbonyl, $(C_3-C_6)$ alkenyl, $(C_3-C_6)$alkynyl or aryl;
$R^4$ is hydrogen or $(C_1-C_6)$alkyl;
$R^5$ is hydrogen, hydroxy, $(C_1-C_6)$alkoxy, $(C_1-C_6)$ alkanoyloxy or aryl $(C_1-C_6)$alkyl;
$R^6$ is hydrogen, $(C_1-C_6)$alkyl, aryl, aryl$(C_1-C_6)$alkyl, $(C_1-C_6)$alkylcarbonyl, aryl$(C_1-C_6)$alkylcarbonyl or $(C_1-C_6)$alkoxycarbonyl;
$R^{11}$ is $(C_1-C_6)$alkyl, $(C_1-C_6)$alkoxy, hydroxy, halogen, nitro or trifluoro;
m is an integer from 2 to 7;
n is an integer from 0 to 3; and
r is an integer from 0 to 2.

In one preferred embodiment of this class are compounds of the formula

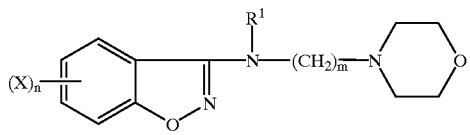

wherein
X is hydrogen, $(C_1-C_6)$alkyl, $(C_1-C_6)$alkoxy, $(C_1-C_6)$ alkoxymethyleneoxy, aryl$(C_1-C_6)$alkoxy, halo, hydroxy, $(C_1-C_6)$alkanoylamino, aminocarbonyloxy, $(C_1-C_{10})$ alkylaminocarbonyloxy, di$(C_1-C_{10})$ alkylaminocarbonyloxy, aryl$(C_1-C_{10})$ alkylaminocarbonyloxy, $(C_1-C_6)$alkoxycarbonyloxy, tetrahydroisoquinolylcarbonyloxyl or aryl$(C_1-C_6)$ alkylcarbonyloxy;
$R^1$ is hydrogen, $(C_1-C_6)$alkyl, aryl$(C_1-C_6)$alkyl, $(C_1-C_6)$ alkoxycarbonyl, aryloxycarbonyl, aryl$(C_1-C_6)$ alkoxycarbonyl, aminocarbonyl, $(C_1-C_6)$ alkylaminocarbonyl, or di$(C_1-C_6)$alkylaminocarbonyl;
m is an integer from 2 to 7;
n is an integer from 0 to 3; and
pharmaceutically acceptable acid addition salts thereof and optical and geometric isomers or racemic mixtures thereof.
Preferably in this embodiment
X is hydrogen, hydroxy, halo, $(C_1-C_6)$alkyl, $(C_1-C_6)$alkoxy, $(C_1-C_8)$alkylaminocarbonyloxy, tetrahydroisoquinolylcarbonyloxy, di$(C_1-C_8)$ alkylaminocarbonyloxy or aryl$(C_1-C_6)$ alkylaminocarbonyloxy;
$R^1$ is hydrogen or $(C_1-C_6)$alkyl;

n is 1 or 2; and
m is 2, 3 or 4.
Most preferably
X is hydrogen, 5-hydroxy, 5-methoxy, 5-methylaminocarbonyloxy, 5-dimethylaminocarbonyloxy, 5-methylethylaminocarbonyloxy, 5-bromo, 7-bromo, 5-phenylmethylaminocarbonyloxy, 6-hydroxy, 6-methoxy, 6-methylaminocarbonyloxy, 6-methylethylaminocarbonyloxy, 6-dimethylaminocarbonyloxy, 6-phenylmethylaminocarbonyloxy, 5-hexylaminocarbonyloxy, 5-heptylaminocarbonyloxy, 5-tetrahydroisoquinol-2-ylcarbonyloxy, 6-hexylaminocarbonyloxy, 6-heptylaminocarbonyloxy or 6-tetrahydroisoquinol-2-ylcarbonyloxy;
$R^1$ is hydrogen or methyl; and
m is 2.

In another preferred embodiment of this class are compounds of the formula

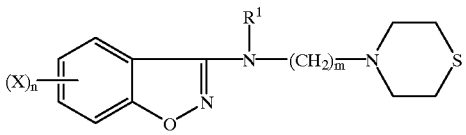

wherein
X is hydrogen, $(C_1-C_6)$alkyl, $(C_1-C_6)$alkoxy, $(C_1-C_6)$ alkoxymethyleneoxy, aryl$(C_1-C_6)$alkoxy, halo, hydroxy, $(C_1-C_6)$alkanoylamino, aminocarbonyloxy, $(C_1-C_{10})$ alkylaminocarbonyloxy, di$(C_1-C_{10})$ alkylaminocarbonyloxy, aryl$(C_1-C_{10})$ alkylaminocarbonyloxy, $(C_1-C_6)$alkoxycarbonyloxy, tetrahydroisoquinolylcarbonyloxy or aryl$(C_1-C_6)$ alkylcarbonyloxy;
$R^1$ is hydrogen, $(C_1-C_6)$alkyl, aryl$(C_1-C_6)$alkyl, $(C_1-C_6)$ alkoxycarbonyl, aryloxycarbonyl, aryl$(C_1-C_6)$ alkoxycarbonyl, aminocarbonyl, $(C_1-C_6)$ alkylaminocarbonyl, or di$(C_1-C_6)$alkylaminocarbonyl;
m is an integer from 2 to 7;
n is an integer from 0 to 3; and
pharmaceutically acceptable acid addition salts thereof and optical and geometric isomers or racemic mixtures thereof.
Preferably in this embodiment
X is hydrogen, hydroxy, halo, $(C_1-C_6)$alkyl, $(C_1-C_6)$alkoxy, $(C_1-C_6)$alkoxymethyleneoxy, $(C_1-C_8)$ alkylaminocarbonyloxy, tetrahydroisoquinolylcarbonyloxy, di$(C_1-C_8)$ alkylaminocarbonyloxy or aryl$(C_1-C_6)$ alkylaminocarbonyloxy;
$R^1$ is hydrogen or $(C_1-C_6)$alkyl;
n is 1 or 2; and
m is 2, 3 or 4.
Most preferably
X is hydrogen, 5-hydroxy, 5-methoxy, 5-methylaminocarbonyloxy, 5-dimethylaminocarbonyloxy, 5-methylethylaminocarbonyloxy, 5-bromo, 7-bromo, 6-methoxymethoxy, 5-phenylmethylaminocarbonyloxy, 6-hydroxy, 6-methoxy, 6-methylaminocarbonyloxy, 6-methylethylaminocarbonyloxy, 6-dimethylaminocarbonyloxy, 6-phenylmethylaminocarbonyloxy, 5-hexylaminocarbonyloxy, 5-heptylaminocarbonyloxy, 5-tetrahydroisoquinol-2-ylcarbonyloxy,
6-hexylaminocarbonyloxy, 6-heptylaminocarbonyloxy or
6-tetrahydroisoquinol-2-ylcarbonyloxy;
$R^1$ is hydrogen or methyl; and
m is 2.

In yet another preferred embodiment of this class are compounds of the formula

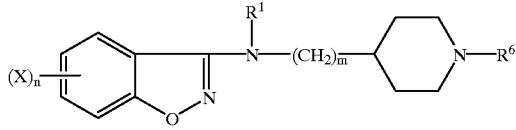

wherein

X is hydrogen, $(C_1-C_6)$alkyl, $(C_1-C_6)$alkoxy, $(C_1-C_6)$alkoxymethyleneoxy, aryl$(C_1-C_6)$alkoxy, halo, hydroxy, $(C_1-C_6)$alkanoylamino, aminocarbonyloxy, $(C_1-C_{10})$alkylaminocarbonyloxy, di$(C_1-C_{10})$alkylaminocarbonyloxy, aryl$(C_1-C_{10})$alkylaminocarbonyloxy, $(C_1-C_6)$alkoxycarbonyloxy, tetrahydroisoquinolylcarbonyloxy or aryl$(C_1-C_6)$alkylcarbonyloxy;

$R^1$ is hydrogen, $(C_1-C_6)$alkyl, aryl$(C_1-C_6)$alkyl, $(C_1-C_6)$alkoxycarbonyl, aryloxycarbonyl, aryl$(C_1-C_6)$alkoxycarbonyl, aminocarbonyl, $(C_1-C_6)$alkylaminocarbonyl, or di$(C_1-C_6)$alkylaminocarbonyl;

$R^6$ is hydrogen, $(C_1-C_6)$alkyl, aryl, aryl$(C_1-C_6)$alkyl, $(C_1-C_6)$alkylcarbonyl, aryl$(C_1-C_6)$alkylcarbonyl or $(C_1-C_6)$alkoxycarbonyl;

m is an integer from 2 to 7;
n is an integer from 0 to 3; and pharmaceutically acceptable acid addition salts thereof and optical and geometric isomers or racemic mixtures thereof.

Preferably in this embodiment

X is hydrogen, hydroxy, halo, $(C_1-C_6)$alkyl, $(C_1-C_6)$alkoxy, $(C_1-C_8)$alkylaminocarbonyloxy, di$(C_1-C_8)$alkylaminocarbonyloxy, tetrahydroisoquinolylcarbonyloxy or aryl$(C_1-C_6)$alkylaminocarbonyloxy;

$R^1$ is hydrogen or $(C_1-C_6)$alkyl;
$R^6$ is $(C_1-C_6)$alkyl or aryl$(C_1-C_6)$alkyl;
n is 1 to 2; and
m is 2, 3 or 4.

Most preferably

X is hydrogen, 5-hydroxy, 5-methoxy, 5-methylaminocarbonyloxy, 5-dimethylacabonyloxy, 5-methylethylaminocarbonyloxy, 5-bromo, 7-bromo, 5-phenylmethylaminocarbonyloxy, 6-hydroxy, 6-methoxy, 6-dimethylaminocarbonyloxy, 5-heptylaminocarbonyloxy, 6-methylaminocarbonyloxy, 6-methylethylaminocarbonyloxy, 6-phenylmethylaminocarbonyloxy, 5-hexylaminocarbonyloxy, 5-tetrahydroisoquinol-2-ylcarbonyloxy, 6-hexylaminocarbonyloxy, 6-heptylaminocarbonyloxy or 6-tetrahydroisoquinol-2-ylcarbonyloxy;

$R^1$ is hydrogen or methyl;
$R^6$ is phenylmethyl; and
m is 2.

In another preferred embodiment of this class are compounds of the formula

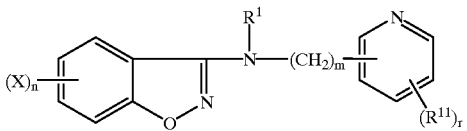

wherein

X is hydrogen, $(C_1-C_6)$alkyl, $(C_1-C_6)$alkoxy, $(C_1-C_6)$alkoxymethyleneoxy, aryl$(C_1-C_6)$alkoxy, halo, hydroxy, $(C_1-C_6)$alkanoylamino, aminocarbonyloxy, $(C_1-C_{10})$alkylaminocarbonyloxy, di$(C_1-C_{10})$alkylaminocarbonyloxy, aryl$(C_1-C_{10})$alkylaminocarbonyloxy, $(C_1-C_6)$alkoxycarbonyloxy, tetrahydroisoquinolylcarbonyloxy or aryl$(C_1-C_6)$alkylcarbonyloxy;

$R^1$ is hydrogen, $(C_1-C_6)$alkyl, aryl$(C_1-C_6)$alkyl, $(C_1-C_6)$alkoxycarbonyl, aryloxycarbonyl, aryl$(C_1-C_6)$alkoxycarbonyl, aminocarbonyl, $(C_1-C_6)$alkylaminocarbonyl, or di$(C_1-C_6)$alkylaminocarbonyl;

$R^{11}$ is $(C_1-C_6)$alkyl, $(C_1-C_6)$alkoxy, hydroxy, halogen, nitro or trifluoro;

m is an integer from 2 to 7;
n is an integer from 0 to 3;
r is an integer from 0 to 2; and pharmaceutically acceptable acid addition salts thereof and optical and geometric isomers or racemic mixtures thereof.

Preferably in this embodiment

X is hydrogen, hydroxy, halo, $(C_1-C_6)$alkyl, $(C_1-C_6)$alkoxy, $(C_1-C_8)$alkylaminocarbonyloxy, tetrahydroisoquinolylcarbonyloxy, di$(C_1-C_8)$alkylaminocarbonyloxy or aryl$(C_1-C_6)$alkylaminocarbonyloxy;

$R^1$ is hydrogen or $(C_1-C_6)$alkyl;
n is 1 to 2; and
m is 2, 3 or 4.

Most preferably

X is hydrogen, 5-hydroxy, 5-methoxy, 5-methylaminocarbonyloxy, 5-dimethylaminocarbonyloxy, 5-methylethylaminocarbonyloxy, 5-bromo, 7-bromo, 5-phenylmethylaminocarbonyloxy, 6-hydroxy, 6-methoxy, 6-methylaminocarbonyloxy, 6-methylethylaminocarbonyloxy, 6-dimethylaminocarbonyloxy, 6-phenylmethylaminocarbonyloxy, 5-hexylaminocarbonyloxy, 5-heptylaminocarbonyloxy, 5-tetrahydroisoquinol-2-ylcarbonyloxy, 6-hexylaminocarbonyloxy, 6-heptylaminocarbonyloxy or 6-tetrahydroisoquinol-2-ylcarbonyloxy;

$R^1$ is hydrogen or methyl; and
m is 2.

In yet another embodiment of this class are compounds of the formula

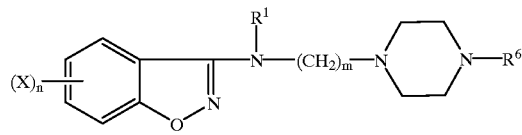

wherein

X is hydrogen, $(C_1-C_6)$alkyl, $(C_1-C_6)$alkoxy, $(C_1-C_6)$alkyloxymethyleneoxy, aryl$(C_1-C_6)$alkoxy, halo, hydroxy, $(C_1-C_6)$alkanoylamino, aminocarbonyloxy, ($C_1$–$C_{10}$)alkylaminocarbonyloxy, di($C_1$–$C_{10}$)alkylaminocarbonyloxy, aryl($C_1$–$C_{10}$)alkylaminocarbonyloxy, ($C_1$–$C_{10}$)alkylaminocarbonyloxy, ($C_1$–$C_6$)alkoxycarbonyloxy, tetrahydroisoquinolylcarbonyloxy or aryl($C_1$–$C_6$)alkylcarbonyloxy;

$R^1$ is hydrogen, ($C_1$–$C_6$)alkyl, aryl($C_1$–$C_6$)alkyl, ($C_1$–$C_6$)alkoxycarbonyl, aryloxycarbonyl, aryl($C_1$–$C_6$)alkoxycarbonyl, aminocarbonyl, ($C_1$–$C_6$)alkylaminocarbonyl, or di($C_1$–$C_6$)alkylaminocarbonyl;

$R^6$ is hydrogen, ($C_1$–$C_6$)alkyl, aryl, aryl($C_1$–$C_6$)alkyl, ($C_1$–$C_6$)alkylcarbonyl, aryl($C_1$–$C_6$)alkylcarbonyl or ($C_1$–$C_6$)alkoxycarbonyl;

m is an integer from 2 to 7;
n is an integer from 0 to 3; and
pharmaceutically acceptable acid addition salts thereof and optical and geometric isomers or racemic mixtures thereof.

Preferably in this embodiment

X is hydrogen, hydroxy, halo, ($C_1$–$C_6$)alkyl, ($C_1$–$C_6$)alkoxy, ($C_1$–$C_8$)alkylaminocarbonyloxy, tetrahydroisoquinolylcarbonyloxy, di($C_1$–$C_8$)alkylaminocarbonyloxy or aryl($C_1$–$C_6$)aminocarbonyloxy;

$R^1$ is hydrogen or ($C_1$–$C_6$)alkyl;
$R^6$ is aryl($C_1$–$C_6$)alkyl;
n is 1 or 2; and
m is 2, 3 or 4.

Preferably in this embodiment

X is hydrogen, 5-hydroxy, 5-methoxy, 5-methylaminocarbonyloxy, 5-dimethylaminocarbonyloxy, 5-methylethylaminocarbonyloxy, 5-bromo, 7-bromo, 5-phenylmethylaminocarbonyloxy, 6-hydroxy, 6-methoxy, 6-methylaminocarbonyloxy, 6-methylethylaminocarbonyloxy, 6-dimethylaminocarbonyloxy, 6-phenylmethylaminocarbonyloxy, 5-tetrahydroisoquinol-2-ylcarbonyloxy, 6-hexylaminocarbonyloxy, 6-heptylaminocarbonyloxy or 6-tetrahydroisoquinol-2-ylcarbonyloxy;

$R^1$ is hydrogen or methyl;
$R_6$ is phenylmethyl; and
m is 2.

In another embodiment of this class are compounds of the formula

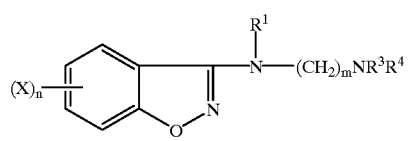

wherein

X is hydrogen, ($C_1$–$C_6$)alkyl, ($C_1$–$C_6$)alkoxy, ($C_1$–$C_6$)alkoxymethyleneoxy, aryl($C_1$–$C_6$)alkoxy, halo, hydroxy, ($C_1$–$C_6$)alkanoylamino, aminocarbonyloxy, ($C_1$–$C_{10}$)alkylaminocarbonyloxy, di($C_1$–$C_{10}$)alkylaminocarbonyloxy, aryl($C_1$–$C_{10}$)alkylaminocarbonyloxy, ($C_1$–$C_6$)alkoxycarbonyloxy, tetrahydroisoquinolylcarbonyloxy or aryl($C_1$–$C_6$)alkylcarbonyloxy;

$R^1$ is hydrogen, ($C_1$–$C_6$)alkyl, aryl($C_1$–$C_6$)alkyl, ($C_1$–$C_6$)alkoxycarbonyl, aryloxycarbonyl, aryl($C_1$–$C_6$)alkoxycarbonyl, aminocarbonyl, ($C_1$–$C_6$)alkylaminocarbonyl, or di($C_1$–$C_6$)alkylaminocarbonyl;

$R^3$ is hydrogen, ($C_1$–$C_6$)alkyl, aryl($C_1$–$C_6$)alkyl, ($C_1$–$C_6$)alkylcarbonyl, ($C_1$–$C_6$)alkoxycarbonyl, ($C_3$–$C_6$)alkenyl, ($C_3$–$C_6$)alkynoyl, aryl, amino($C_1$–$C_6$)alkyl, mono($C_1$–$C_6$)alkylamino, ($C_1$–$C_6$)alkyl or di($C_1$–$C_6$)alkylamino($C_1$–$C_6$)alkyl;

$R^4$ is hydrogen or ($C_1$–$C_6$)alkyl;
m is an integer from 2 to 7;
n is an integer from 0 to 3; and
pharmaceutically acceptable acid addition salts thereof and optical and geometric isomers or racemic mixtures thereof.

Preferably in this embodiment

X is hydrogen, hydroxy, halo, ($C_1$–$C_6$)alkyl, ($C_1$–$C_6$)alkoxy, ($C_1$–$C_8$)alkylaminocarbonyloxy, tetrahydroisoquinolylcarbonyloxy, di($C_1$–$C_8$)alkylaminocarbonyloxy or aryl($C_1$–$C_6$)alkylaminocarbonyloxy;

$R^1$ is hydrogen or ($C_1$–$C_6$)alkyl;
$R^3$ is ($C_1$–$C_6$)alkyl;
$R^4$ is hydrogen;
n is 1 or 2; and
m is 2, 3 or 4, Most preferably X is hydrogen, 5-hydroxy, 5-methoxy, 5-methylaminocarbonyloxy, 5-dimethylaminocarbonyloxy, 5-methylethylaminocarbonyloxy, 5-bromo, 7-bromo, 5-phenylmethylaminocarbonyloxy, 6-hydroxy, 6-methoxy, 6-methylaminocarbonyloxy, 6-methylethylaminocarbonyloxy, 6-dimethylaminocarbonyloxy, 6-phenylmethylaminocarbonyloxy, 5-hexylaminocarbonyloxy, 5-heptylaminocarbonyloxy, 5-tetrahydroisoquinol-2-ylcarbonyloxy, 6-hexylaminocarbonyloxy, 6-heptylaminocarbonyloxy or 6-tetrahydroisoquinol-2-ylcarbonyloxy;

$R^1$ is hydrogen or methyl;
$R^3$ is methyl;
$R^4$ is hydrogen; and
m is 2.

In another class of compounds of this invention are compounds of the formula

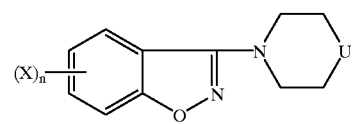

wherein

X is as defined above; and

U is N-$R^7$, ($CH_2$)$_s$amino where the amino group is unsubstituted or mono or disubstituted with ($C_1$–$C_6$)alkyl or aryl($C_1$–$C_6$)alkyl; and s is an integer from 1 to 6; and $R^7$ is hydrogen, ($C_1$–$C_6$)alkyl, phenyl, phenyl($C_1$–$C_6$)alkenyl, ($C_3$–$C_6$)alkynyl, pyridyl, pyrimidyl, pyridazinyl, pyrazinyl or quinolinyl.

In one preferred embodiment of this class are compounds of the formula

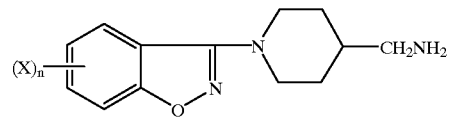

wherein

X is hydrogen, ($C_1$–$C_6$)alkyl, ($C_1$–$C_6$)alkoxy, ($C_1$–$C_6$)alkoxymethyleneoxy, aryl($C_1$–$C_6$)alkoxy, halo, hydroxy, ($C_1$–$C_6$)alkanoylamino, aminocarbonyloxy, ($C_1$–$C_{10}$)

alkylaminocarbonyloxy, di($C_1$-$C_{10}$) alkylaminocarbonyloxy, aryl($C_1$-$C_{10}$) alkylaminocarbonyloxy, ($C_1$-$C_6$)alkoxycarbonyloxy, tetrahydroisoquinolylcarbonyloxy or aryl($C_1$-$C_6$) alkylcarbonyloxy; and n is an integer from 0 to 3; and pharmaceutically acceptable acid addition salts thereof and optical and geometric isomers or racemic mixtures thereof.

Preferably in this embodiment.

X is hydrogen, hydroxy, halo, ($C_1$-$C_6$)alkyl, ($C_1$-$C_6$)alkoxy, ($C_1$-$C_8$)alkylaminocarbonyloxy, tetrahydroisoquinolylcarbonyloxy, di($C_1$-$C_8$)alkylaminocarbonyloxy or aryl($C_1$-$C_6$) alkylaminocarbonyloxy; and n is 1 or 2;

Most preferably

X is hydrogen, 5-hydroxy, 5-methoxy, 5-methylaminocarbonyloxy, 5-dimethylaminocarbonyloxy, 5-methylethylaminocarbonyloxy, 5-bromo, 7-bromo, 5-phenylmethylaminocarbonyloxy, 6-hydroxy, 6-methoxy, 6-methylaminocarbonyloxy, 6-methylethylaminocarbonyloxy, 6-dimethylaminocarbonyloxy, 6-phenylmethylaminocarbonyloxy, 5-hexylaminocarbonyloxy, 5-heptylaminocarbonyloxy, 5-tetrahydroisoquinol-2-ylcarbonyloxy, 6-hexylaminocarbonyloxy, 6-heptylaminocarbonyloxy or 6-tetrahydroisoquinol-2-ylcarbonyloxy.

In yet another embodiment are compounds of the formula

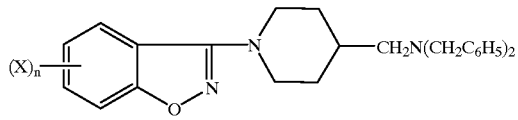

wherein

X is hydrogen, ($C_1$-$C_6$)alkyl, ($C_1$-$C_6$)alkoxy, ($C_1$-$C_6$)alkoxymethyleneoxy, aryl($C_1$-$C_6$)alkoxy, halo, hydroxy, ($C_1$-$C_6$)alkanoylamino, aminocarbonyloxy, ($C_1$-$C_{10}$)alkylaminocarbonyloxy, di($C_1$-$C_{10}$)alkylaminocarbonyloxy, aryl($C_1$-$C_{10}$)alkylaminocarbonyloxy, ($C_1$-$C_6$)alkoxycarbonyloxy, tetrahydroisoquinolylcarbonyloxy or aryl($C_1$-$C_6$) alkylcarbonyloxy;

n is an integer from 0 to 3; and pharmaceutically acceptable acid addition salts thereof and optical and geometric isomers or racemic mixtures thereof.

Preferably in this embodiment

X is hydrogen, hydroxy, halo, ($C_1$-$C_6$)alkyl, ($C_1$-$C_6$)alkoxy, ($C_1$-$C_8$)alkylaminocarbonyloxy, tetrahydroisoquinolylcarbonyloxy or di($C_1$-$C_8$)alkylaminocarbonyloxy, aryl ($C_1$-$C_6$)alkylaminocarbonyloxy; and n is 1 or 2.

Most preferably

X is hydrogen, 5-hydroxy, 5-methoxy, 5-methylaminocarbonyloxy, 5-dimethylaminocarbonyloxy, 5-methylethylaminocarbonyloxy, 5-bromo, 7-bromo, 5-phenylmethylaminocarbonyloxy, 6-hydroxy, 6-methoxy, 6-methylaminocarbonyloxy, 6-methylethylaminocarbonyloxy, 6-dimethylaminocarbonyloxy, 6-phenylmethylaminocarbonyloxy, 5-hexylaminocarbonyloxy, 5-heptylaminocarbonyloxy, 5-tetrahydroisoquinol-2-ylcarbonyloxy, 6-hexylaminocarbonyloxy, 6-heptylaminocarbonyloxy or 6-tetrahydroisoquinol-2-ylcarbonyloxy.

In another embodiment of this class are compounds of the formula

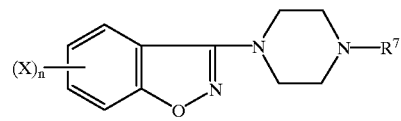

wherein X and $R^7$ are as defined above.

In a preferred embodiment of this class are compounds of the formula

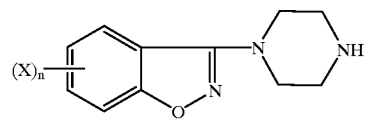

wherein

X is hydrogen, ($C_1$-$C_6$)alkyl, ($C_1$-$C_6$)alkoxy, ($C_1$-$C_6$)alkoxymethyleneoxy, aryl($C_1$-$C_6$)alkoxy, halo, hydroxy, ($C_1$-$C_6$)alkanoylamino, aminocarbonyloxy, ($C_1$-$C_{10}$)alkylaminocarbonyloxy, di($C_1$-$C_{10}$)alkylaminocarbonyloxy, aryl($C_1$-$C_{10}$)alkylaminocarbonyloxy, ($C_1$-$C_6$)alkoxycarbonyloxy, or tetrahydroisoquinolylcarbonyloxy or aryl($C_1$-$C_6$) alkylcarbonyloxy;

n is an integer from 0 to 3; and pharmaceutically acceptable acid addition salts thereof and optical and geometric isomers or racemic mixtures thereof.

Preferably in this embodiment

X is hydrogen, hydroxy, halo, ($C_1$-$C_6$)alkyl, ($C_1$-$C_6$)alkoxy, ($C_1$-$C_8$) alkylaminocarbonyloxy, tetrahydroisoquinolylcarbonyloxy or di($C_1$-$C_8$)alkylaminocarbonyloxy, aryl ($C_1$-$C_6$)alkylaminocarbonyloxy; and n is 1 or 2.

Most preferably

X is hydrogen, 5-hydroxy, 5-methoxy, 5-methylaminocarbonyloxy, 5-dimethylaminocarbonyloxy, 5-methylethylaminocarbonyloxy, 5-bromo, 7-bromo, 5-phenylmethylaminocarbonyloxy, 6-hydroxy, 6-methoxy, 6-methylaminocarbonyloxy, 6-methylethylaminocarbonyloxy, 6-dimethylaminocarbonyloxy, 6-phenylmethylaminocarbonyloxy, 5-hexylaminocarbonyloxy, 5-heptylaminocarbonyloxy, 5-tetrahydroisoquinol-2-ylcarbonyloxy, 6-hexylaminocarbonyloxy, 6-heptylaminocarbonyloxy or 6-tetrahydroisoquinol-2-ylcarbonyloxy.

In one preferred embodiment of this class are compounds of the formula

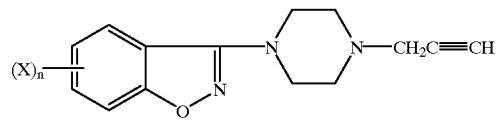

wherein

X is hydrogen, ($C_1$-$C_6$)alkyl, ($C_1$-$C_6$)alkoxy, ($C_1$-$C_6$)alkoxymethyleneoxy, aryl($C_1$-$C_6$)alkoxy, halo, hydroxy, ($C_1$-$C_6$)alkanoylamino, aminocarbonyloxy, ($C_1$-$C_{10}$)alkylaminocarbonyloxy, di($C_1$-$C_{10}$)

alkylaminocarbonyloxy, aryl($C_1$-$C_{10}$) alkylaminocarbonyloxy, ($C_1$-$C_6$)alkoxycarbonyloxy, tetrahydroisoquinolylcarbonyloxy or aryl($C_1$-$C_6$) alkylcarbonyloxy; and n is an integer from 0 to 3; and pharmaceutically acceptable acid addition salts thereof and optical and geometric isomers or racemic mixtures thereof.

Preferably in this embodiment

X is hydrogen, hydroxy, halo, ($C_1$-$C_6$)alkyl, ($C_1$-$C_6$)alkoxy, ($C_1$-$C_8$)alkylaminocarbonyloxy, tetrahydroisoquinolylcarbonyloxy di($C_1$-$C_8$)alkylaminocarbonyloxy or aryl ($C_1$-$C_6$)alkylaminocarbonyloxy; and n is 1 or 2.

Most preferably

X is hydrogen, 5-hydroxy, 5-methoxy, 5-methylaminocarbonyloxy, 5-dimethylaminocarbonyloxy, 5-methylethylaminocarbonyloxy, 5-bromo, 7-bromo, 5-phenylmethylaminocarbonyloxy, 6-hydroxy, 6-methoxy, 6-methylaminocarbonyloxy, 6-methylethylaminocarbonyloxy, 6-dimethylaminocarbonyloxy, 6-phenylmethylaminocarbonyloxy, 5-hexylaminocarbonyloxy, 5-heptylaminocarbonyloxy, 5-tetrahydroisoquinol-2-ylcarbonyloxy, 6-hexylaminocarbonyloxy, 6-heptylaminocarbonyloxy or 6-tetrahydroisoquinol-2-ylcarbonyloxy.

In yet another embodiment are compounds of the formula

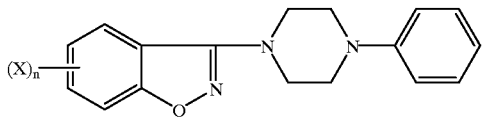

wherein

X is hydrogen, ($C_1$-$C_6$)alkyl, ($C_1$-$C_6$)alkoxy, ($C_1$-$C_6$)alkoxymethyleneoxy, aryl($C_1$-$C_6$)alkoxy, halo, hydroxy, ($C_1$-$C_6$)alkanoylamino, aminocarbonyloxy, ($C_1$-$C_{10}$) alkylaminocarbonyloxy, di($C_1$-$C_{10}$) alkylaminocarbonyloxy, aryl($C_1$-$C_{10}$) alkylaminocarbonyloxy, ($C_1$-$C_6$)alkylcarbonyloxy, tetrahydroisoquinolylcarbonyloxy or aryl($C_1$-$C_6$) alkylcarbonyloxy; and n is an integer from 0 to 3; and pharmaceutically acceptable acid addition salts thereof and optical and geometric isomers or racemic mixtures thereof.

Preferably in this embodiment

X is hydrogen, hydroxy, halo, ($C_1$-$C_6$)alkyl, ($C_1$-$C_6$)alkoxy, ($C_1$-$C_8$)alkylaminocarbonyloxy, tetrahydroisoquinolylcarbonyloxy, di($C_1$-$C_8$) alkylaminocarbonyloxy or aryl($C_1$-$C_6$) alkylaminocarbonyloxy; and n is 1 or 2.

Most preferably

X is hydrogen, 5-hydroxy, 5-methoxy, 5-methylaminocarbonyloxy, 5-dimethylaminocarbonyloxy, 5-methylethylaminocarbonyloxy, 5-bromo, 7-bromo, 5-phenylmethylaminocarbonyloxy, 6-hydroxy, 6-methoxy, 6-methylaminocarbonyloxy, 6-methylethylaminocarbonyloxy, 6-dimethylaminocarbonyloxy, 6-phenylmethylaminocarbonyloxy, 5-hexylaminocarbonyloxy, 5-heptylaminocarbonyloxy, 5-tetrahydroisoquinol-2-ylcarbonyloxy, 6-hexylaminocarbonyloxy, 6-haptylaminocarbonyloxy or 6-tetrahydroisoquinol-2-ylcarbonyloxy.

In one preferred embodiment of this class are compounds of the formula

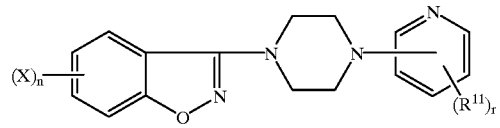

wherein

X is hydrogen, ($C_1$-$C_6$)alkyl, ($C_1$-$C_6$)alkoxy, ($C_1$-$C_6$) alkoxymethyleneoxy, aryl($C_1$-$C_6$)alkoxy, halo, hydroxy, ($C_1$-$C_6$)alkanoylamino, aminocarbonyloxy, ($C_1$-$C_{10}$) alkylaminocarbonyloxy, di($C_1$-$C_{10}$) alkylaminocarbonyloxy, aryl($C_1$-$C_{10}$) alkylaminocarbonyloxy, ($C_1$-$C_6$)alkoxycarbonyloxy, or tetrahydroisoquinolylcarbonyloxy or aryl($C_1$-$C_6$) alkylcarbonyloxy;

$R^{11}$ is ($C_1$-$C_6$)alkyl, ($C_1$-$C_6$)alkoxy, hydroxy, halogen, nitro or trifluoromethyl;

n is an integer from 0 to 3;

r is an integer from 0 to 2; and pharmaceutically acceptable acid addition salts thereof and optical and geometric isomers or racemic mixtures thereof.

Preferably in this embodiment

X is hydrogen, hydroxy, halo, ($C_1$-$C_6$)alkyl, ($C_1$-$C_6$)alkoxy, ($C_1$-$C_8$) alkylaminocarbonyloxy, tetrahydroisoquinolylcarbonyloxy, di($C_1$-$C_8$) alkylaminocarbonyloxy or aryl($C_1$-$C_6$) alkylaminocarbonyloxy;

$R^{11}$ is ($C_1$-$C_6$)alkyl or halogen;

n is 1 or 2; and r is 0 or 1.

Most preferably

X is hydrogen, 5-hydroxy, 5-methoxy, 5-methylaminocarbonyloxy, 5-dimethylaminocarbonyloxy, 5-methylethylaminocarbonyloxy, 5-bromo, 7-bromo, 5-phenylmethylaminocarbonyloxy, 6-hydroxy, 6-methoxy, 6-methylaminocarbonyloxy, 6-methylethylaminocarbonyloxy, 6-dimethylaminocarbonyloxy, 6-phenylmethylaminocarbonyloxy, 5-hexylaminocarbonyloxy, 5-heptylaminocarbonyloxy, 5-tetrahydroisoquinol-2-ylcarbonyloxy, 6-hexylaminocarbonyloxy, 6-heptylaminocarbonyloxy or 6-tetrahydroisoquinol-2-ylcarbonyloxy.

$R^{11}$ is methyl; and r is 0 or 1.

In yet another embodiment are compounds of the formula

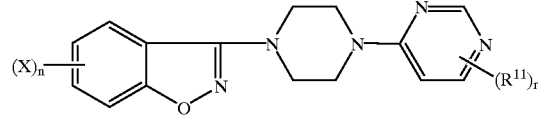

wherein

X is hydrogen, ($C_1$-$C_6$)alkyl, ($C_1$-$C_6$)alkoxy, ($C_1$-$C_6$) alkoxymethyleneoxy, aryl($C_1$-$C_6$)alkoxy, halo, hydroxy, ($C_1$-$C_6$)alkanoylamino, aminocarbonyloxy, ($C_1$-$C_{10}$) alkylaminocarbonyloxy, di($C_1$-$C_{10}$) alkylaminocarbonyloxy, aryl($C_1$-$C_{10}$) alkylaminocarbonyloxy, ($C_1$-$C_6$)alkoxycarbonyloxy, tetrahydroisoquinolylcarbonyloxy or aryl($C_1$-$C_6$) alkylcarbonyloxy;

$R^{11}$ is halo, $(C_1-C_6)$alkyl, $(C_1-C_6)$alkoxy, hydroxy, nitro or trifluoromethyl;

n is an integer from 0 to 3;

r is an integer from 0 to 2; and pharmaceutically acceptable acid addition salts thereof and optical and geometric isomers or racemic mixtures thereof.

Preferably in this embodiment

X is hydrogen, hydroxy, halo, $(C_1-C_6)$alkyl, $(C_1-C_6)$alkoxy, $(C_1-C_8)$alkylaminocarbonyloxy, tetrahydroisoquinolylcarbonyloxy or di$(C_1-C_8)$alkylaminocarbonyloxy, aryl$(C_1-C_6)$alkylaminocarbonyloxy;

$R^{11}$ is $(C_1-C_6)$alkyl or halo;

n is 1 or 2; and r is 0 or 1.

Most preferably

X is hydrogen, 5-hydroxy, 5-methoxy, 5-methylaminocarbonyloxy, 5-dimethylaminocarbonyloxy, 5-methylethylaminocarbonyloxy, 5-bromo, 7-bromo, 5-phenylmethylaminocarbonyloxy, 6-hydroxy, 6-methoxy, 6-methylaminocarbonyloxy, 6-methylethylaminocarbonyloxy, 6-dimethylaminocarbonyloxy, 6-phenylmethylaminocarbonyloxy, 5-hexylaminocarbonyloxy, 5-heptylaminocarbonyloxy, 5-tetrahydroisoquinol-2-ylcarbonyloxy, 6-hexylaminocarbonyloxy, 6-heptylaminocarbonyloxy or 6-tetrahydroisoquinol-2-ylcarbonyloxy; and $R^{11}$ is 4-chloro.

In another embodiment are compounds of the formula

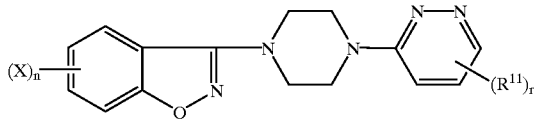

wherein

X is hydrogen, $(C_1-C_6)$alkyl, $C_1-C_6$)alkoxy, $(C_1-C_6)$alkoxymethyleneoxy, aryl$(C_1-C_6)$alkoxy, halo, hydroxy, $(C_1-C_6)$alkanoylamino, aminocarbonyloxy, $(C_1-C_{10})$alkylaminocarbonyloxy, di$(C_1-C_{10})$alkylaminocarbonyloxy, aryl$(C_1-C_{10}$alkylaminocarbonyloxy, $(C_1-C_6)$alkoxycarbonyloxy, tetrahydroisoquinolylcarbonyloxy or aryl$(C_1-C_6)$alkylcarbonyloxy;

$R^{11}$ is halogen, $(C_1-C_6)$alkyl, $(C_1-C_6)$alkoxy, hydroxy, nitro or trifluoromethyl;

n is an integer from 0 to 3;

r is an integer from 0 to 2; and pharmaceutically acceptable acid addition salts thereof and optical and geometric isomers or racemic mixtures thereof.

Preferably in this embodiment

X is hydrogen, hydroxy, halo, $(C_1-C_6)$alkyl, $(C_1-C_6)$alkoxy, $(C_1-C_8)$alkylaminocarbonyloxy, tetrahydroisoquinolylcarbonyloxy, di$(C_1-C_8)$alkylaminocarbonyloxy or aryl$(C_1-C_6)$alkylaminocarbonyloxy;

$R^{11}$ is halogen or $(C_1-C_6)$alkyl;

n is 1 or 2; and r is 0 or 1.

Most preferably

X is hydrogen, 5-hydroxy, 5-methoxy, 5-methylaminocarbonyloxy, 5-dimethylaminocarbonyloxy, 5-methylethylaminocarbonyloxy, 5-bromo, 7-bromo, 5-phenylmethylaminocarbonyloxy, 6-hydroxy, 6-methoxy, 6-methylaminocarbonyloxy, 6-methylethylaminocarbonyloxy, 6-dimethylaminocarbonyloxy, 6-phenylmethylaminocarbonyloxy, 5-hexylaminocarbonyloxy, 5-heptylaminocarbonyloxy, 5-tetrahydroisoquinol-2-ylcarbonyloxy, 6-hexylaminocarbonyloxy, 6-heptylaminocarbonyloxy or 6-tetrahydroisoquinol-2-ylcarbonyloxy; and $R^{11}$ is 5-chloro.

In another embodiment of this class are compounds of the formula

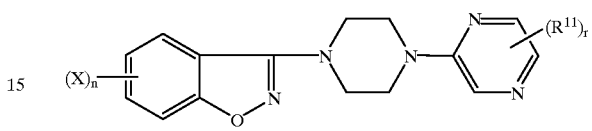

wherein

X is hydrogen, $(C_1-C_6)$alkyl, $(C_1-C_6)$alkoxy, $(C_1-C_6)$alkoxymethyleneoxy, aryl$(C_1-C_6)$alkoxy, halo, hydroxy, $(C_1-C_6)$alkanoylamino, aminocarbonyloxy, $(C_1-C_{10})$alkylaminocarbonyloxy, di$(C_1-C_{10})$alkylaminocarbonyloxy, aryl$(C_1-C_{10})$alkylaminocarbonyloxy, $(C_1-C_6)$alkoxycarbonyloxy, tetrahydroisoquinolylcarbonyloxy or aryl$(C_1-C_6)$alkylcarbonyloxy;

$R^{11}$ is halogen, $(C_1-C_6)$alkyl, $(C_1-C_6)$alkoxy, hydroxy, nitro or trifluoromethyl n is an integer from 0 to 3;

r is an integer from 0 to 2; and pharmaceutically acceptable acid addition salts thereof and optical and geometric isomers or racemic mixtures thereof.

Preferably in this embodiment

X is hydrogen, hydroxy, halo, $(C_1-C_6)$alkyl, $(C_1-C_6)$alkoxy, $(C_1-C_8)$alkylaminocarbonyloxy, tetrahydroisoquinolylcarbonyloxy, di$(C_1-C_8)$alkylaminocarbonyloxy or aryl$(C_1-C_6)$alkylaminocarbonyloxy;

$R^{11}$ is halo or $(C_1-C_6)$alkyl;

n is 1 or 2; and r is 0 or 1.

Most preferably

X is hydrogen, 5-hydroxy, 5-methoxy, 5-methylaminocarbonyloxy, 5-dimethylaminocarbonyloxy, 5-methylethylaminocarbonyloxy, 5-bromo, 7-bromo, 5-phenylmethylaminocarbonyloxy, 6-hydroxy, 6-methoxy, 6-methylaminocarbonyloxy, 6-methylethylaminocarbonyloxy, 6-dimethylaminocarbonyloxy, 6-phenylmethylaminocarbonyloxy, 5-hexylaminocarbonyloxy, 5-heptylaminocarbonyloxy, 5-tetrahydroisoquinol-2-ylcarbonyloxy, 6-hexylaminocarbonyloxy, 6-heptylaminocarbonyloxy or 6-tetrahydroisoquinol-2-ylcarbonyloxy; and $R^{11}$ is 5-chloro.

In another embodiment are compounds of the formula

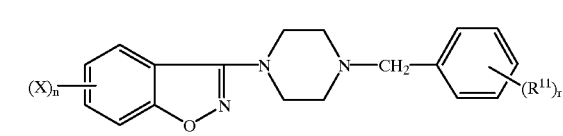

wherein

X is hydrogen, $(C_1-C_6)$alkyl, $(C_1-C_6)$alkoxy, $(C_1-C_6)$alkoxymethyleneoxy, aryl$(C_1-C_6)$alkoxy, halo, hydroxy, ($C_1$-$C_6$)alkanoylamino, aminocarbonyloxy, ($C_1$-$C_{10}$) alkylaminocarbonyloxy, di($C_1$-$C_{10}$) alkylaminocarbonyloxy, aryl($C_1$-$C_{10}$) alkylaminocarbonyloxy, ($C_1$-$C_6$)alkoxycarbonyloxy, tetrahydroisoquinolylcarbonyloxy or aryl($C_1$-$C_6$) alkylcarbonyloxy;

$R^{11}$ is halo, ($C_1$-$C_6$)alkyl, ($C_1$-$C_6$)alkoxy, hydroxy, nitro or trifluoromethyl;

n is an integer from 0 to 3;

r is an integer from 0 to 2; and pharmaceutically acid addition salts thereof and optical and geometric isomers or racemic mixtures thereof.

Preferably in this embodiment

X is hydrogen, hydroxy, halo, ($C_1$-$C_6$)alkyl, ($C_1$-$C_6$)alkoxy, ($C_1$-$C_8$)alkylaminocarbonyloxy, tetrahydroisoquinolylcarbonyloxy, di($C_1$-$C_8$) alkylaminocarbonyloxy or aryl($C_1$-$C_6$) alkylaminocarbonyloxy;

n is 1 or 2; and r is 0 or 1.

Most preferably

X is hydrogen, 5-hydroxy, 5-methoxy, 5-methylaminocarbonyloxy, 5-dimethylaminocarbonyloxy, 5-isopropylaminocarbonyloxy, 5-bromo, 7-bromo, 5-phenylmethylaminocarbonyloxy, 6-hydroxy, 6-methoxy, 6-methylaminocarbonyloxy, 6-methylethylaminocarbonyloxy, 6-dimethylaminocarbonyloxy, 6-phenylmethylaminocarbonyloxy, 5-hexylaminocarbonyloxy, 5-heptylaminocarbonyloxy, 5-tetrahydroisoquinol-2-ylcarbonyloxy, 6-hexylaminocarbonyloxy, 6-heptylaminocarbonyloxy or 6-tetrahydroisoquinol-2-ylcarbonyloxy; and r is 0 or 1; and $R^{11}$ is methyl.

In yet another embodiment are compounds of the formula

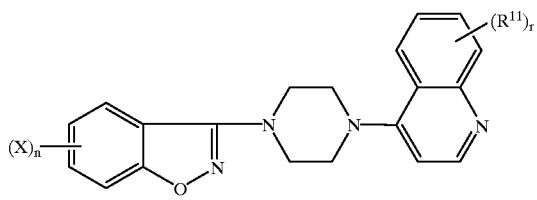

wherein

X is hydrogen, ($C_1$-$C_6$)alkyl, ($C_1$-$C_6$)alkoxy, ($C_1$-$C_6$) alkoxymethyleneoxy, aryl($C_1$-$C_6$)alkoxy, halo, hydroxy, ($C_1$-$C_6$)alkanoylamino, aminocarbonyloxy, ($C_1$-$C_{10}$) alkylaminocarbonyloxy, di($C_1$-$C_{10}$) alkylaminocarbonyloxy, aryl($C_1$-$C_{10}$) alkylaminocarbonyloxy, ($C_1$-$C_6$)alkoxycarbonyloxy, tetrahydroisoquinolylcarbonyloxy or aryl($C_1$-$C_6$) alkylcarbonyloxy;

$R^{11}$ is halogen, ($C_1$-$C_6$)alkyl, ($C_1$-$C_6$)alkoxy, hydroxy, nitro or trifluoromethyl;

n is an integer from 0 to 3;

r is an integer from 0 to 2; and pharmaceutically acceptable acid addition salts thereof and optical and geometric isomers or racemic mixtures thereof.

Preferably in this embodiment

X is hydrogen, hydroxy, halo, ($C_1$-$C_6$)alkyl, ($C_1$-$C_6$)alkoxy, ($C_1$-$C_8$)alkylaminocarbonyloxy, tetrahydroisoquinolylcarbonyloxy, di($C_1$-$C_8$) alkylaminocarbonyloxy or aryl($C_1$-$C_6$) alkylaminocarbonyloxy;

n is 1 or 2; and p is 0 or 1.

Most preferably

X is hydrogen, 5-hydroxy, 5-methoxy, 5-methylaminocarbonyloxy, 5-dimethylaminocarbonyloxy, 5-methylethylaminocarbonyloxy, 5-bromo, 7-bromo, 5-phenylmethylaminocarbonyloxy, 6-hydroxy, 6-methoxy, 6-methylaminocarbonyloxy, 6-methylethylaminocarbonyloxy, 6-dimethylaminocarbonyloxy, 6-phenylmethylaminocarbonyloxy, 5-hexylaminocarbonyloxy, 5-heptylaminocarbonyloxy, 5-tetrahydroisoquinol-2-ylcarbonyloxy, 6-hexylaminocarbonyloxy, 6-heptylaminocarbonyloxy or 6-tetrahydroisoquinol-2-ylcarbonyloxy; and $R^{11}$ is hydrogen, trifluoromethyl or chloro.

Nonlimiting examples of compounds of this invention include:

6-Methoxy-N-methyl-N-[2-(4-morpholinyl)ethyl]-1,2-benzisoxazol-3-amine;

3-[[2-(4-Morpholinyl)-ethyl]methylamino]-1,2-benzisoxazol-6-ol;

3-[[2-(4-Morpholinyl)-ethyl]methylamino]-1,2-benzisoxazol-6-yl methylcarbamate;

3-[[2-(4-Morpholin-yl)ethyl]methylamino]-1,2-benzisoxazol-6-yl phenylmethyl carbamate;

3-[[2-(4-Morpholinyl)-ethyl]methylamino]-1,2-benzisoxazol-6-yl 1-methylethyl-carbamate;

N-methyl-N-[2-(4-morpholinyl)ethyl]-1,2-benzisoxazol-3-amine;

N-[2-(4-Morpholinyl)ethyl]-1,2-benzisoxazol-3-amine;

6-Methoxy-N-[2-(4-morpholinyl)ethyl]-1,2-benzisoxazol-3-amine;

3-[[2-(4-Morpholinyl)ethyl]amino]-1,2-benzisoxazol-6-ol;

3-[[2-(4-Morpholinyl)-ethyl]methylamino]-1,2-benzisoxazol-5-ol;

3-[[2-(4-Morpholinyl)-ethyl]amino]-1,2-benzisoxazol-6-yl methylcarbamate;

3-[[2-(4-Morpholinyl)ethyl]amino]-1,2-benzisoxazol-5-yl methylcarbamate;

6-Chloro-N-[2-(4-morpholinyl)ethyl]-1,2-benzisoxazol-3-amine;

1-Methyl-N-[2-(4-morpholinyl)ethyl]-1,2-indazol-3-amine;

N-Methyl-N-[2-(4-morpholinyl)ethyl]-1,2-benzisothiazol-3-amine;

5-Methoxy-N-[2-(4-morpholinyl)ethyl]-1,2-benzisoxazole-3-amine;

7-Bromo-6-methoxy-N-[2-(4-morpholinyl)ethyl]-1,2-benzisoxazol-3-amine;

5-Bromo-6-methoxy-N-[2-(4-morpholinyl)ethyl]-1,2-benzisoxazol-3-amine;

3-[[2-(4-Morpholinyl)ethyl]amino]-1,2-benzisoxazol-6-yl dimethylcarbamate;

3-[[(Methylamino)carbonyl][2-(4-morpholinyl)ethyl] amino]-1,2-benzisoxazol-6-yl methylcarbamate;

3-[[(Methylamino)carbonyl][2-(4-morpholinyl)ethyl]-amino]-1,2-benzisoxazol-5-yl methylcarbamate;

6-Methoxymethoxy-N-[2-(4-thiomorpholinyl)ethyl]-1,2-benzisoxazol-3-amine;

3-[[2-(4-Thiomorpholinyl)ethyl]amino]-1,2-benzisoxazol-6-ol;

6-Methoxy-N-methyl-N-[2-[4-(1-phenylmethyl) piperdinyl]-1,2-benzisoxazol-3-amine;

7-Bromo-3-[N-methyl, N-2-(4-morpholinyl)ethyl]amino-1,2-benzisoxazol-6-ol; and

7-Bromo-3-[N-methyl, N-2-(4-morpholinyl)ethyl]amino-1,2-benzisoxazol-6-yl dimethylcarbamate.

The compounds of the invention are prepared by one or more of the synthetic routes described below.

Throughout the description of the synthetic schemes, the notations X, $R^1$, $R^2$, $R^3$, $R^4$, $R^5$, $R^6$, $R^7$, $R^8$, $R^9$, $R^{10}$, $R^{11}$ and Y have the respective meanings given above unless otherwise stated or indicated and other notations have the respective meaning defined in their first appearances.

More particularly, as shown in Reaction Scheme A, the chloro compound of Formula III is reacted with an amino compound of Formula IV to yield the compound of Formula V. The reaction is typically carried out neat in a sealed tube at a temperature of from about 100° C. to about 200° C., preferably from about 120° C. to about 180° C., most preferably from about 130° C. to about 150° C. for from about 1.0 hour to about 100 hours, preferably from about 12 hours to about 72 hours, most preferably from about 30 hours to about 60 hours.

When X is alkoxy the compound of Formula V can be treated with acid such as, for example, 48% hydrobromic acid, to yield the corresponding hydroxy compound of Formula VI. The reaction is typically carried out at reflux for from about 1 hour to about 12 hours, preferably from about 2 hours to about 4 hours.

The hydroxy compound of Formula VI is treated with the appropriate isocyanate, carbamoylchloride or carbonyldiimidazole and an amine to obtain the compound of Formula VII wherein $R^7$ is $(C_1-C_{10})$alkyl or aryl$(C_1-C_{10})$alkyl. The reaction is carried in an inert organic solvent such as for example ethyl acetate for about 0.5 hours to about 24 hours, optionally in the presence of a catalyst such as for example copper(I)chloride.

Additionally, the hydroxy compound of Formula VI can be treated with an alkyl, aryl or aralkylhalide, such as for example a benzyl halide, under basic conditions as known in the art to yield the corresponding alkoxy, aryloxy or arylalkoxy compounds of Formula V.

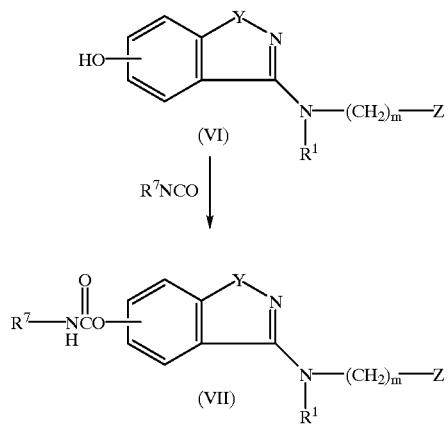

Alternatively, the compounds wherein $R^1$ is hydrogen are synthesized as shown in Reaction Scheme B wherein the amino compound of Formula VIII is reacted with the halo, preferably chloro, compound of Formula IX to obtain the compound of Formula X. The reaction is typically carried out in a polar inert solvent such as dimethylformamide (DMF). The amino compound of Formula VIII is first converted to its corresponding salt, such as, for example, its sodium salt, by reaction with sodium hydride at ambient temperature for about 1 hour. The salt is subsequently reacted without isolation with the halo compound at from about ambient temperature to about 150° C., preferably from about 100° C. to about 130° C. for about 1 hour.

In the case where X is alkoxy, the compound of Formula X is converted to the corresponding hydroxy compound of Formula XI essentially as described for the compound of Formula VI. Subsequent treatment with an isocyanate yields both the monosubstituted compound of Formula XII and the disubstituted compound of Formula XIII. The mixture of the compounds of Formula XII and XIII can be separated by means known in the art, for example, chromatographically.

REACTION SCHEME A

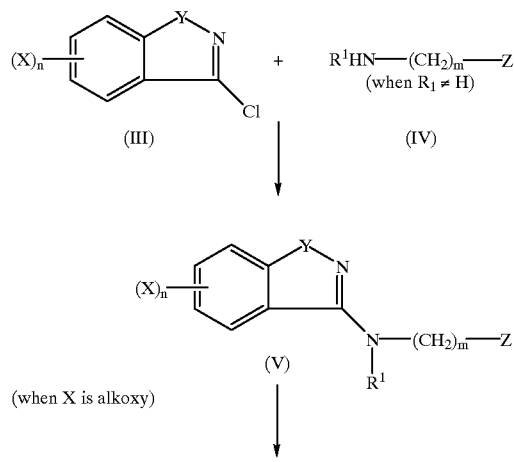

REACTION SCHEME B

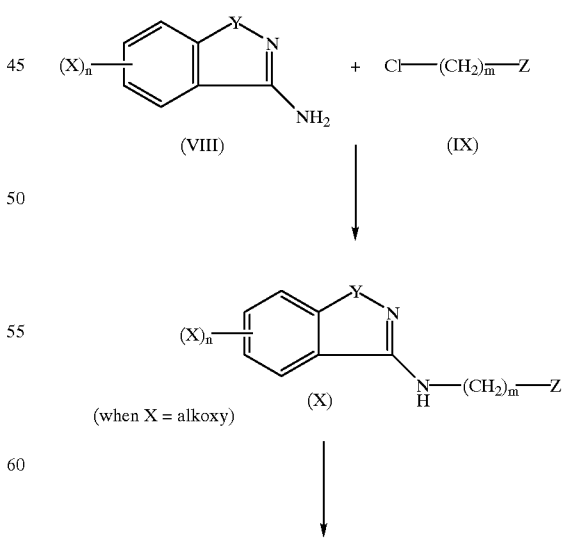

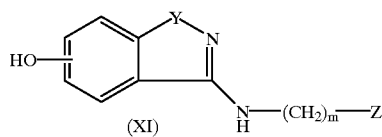
(XI)

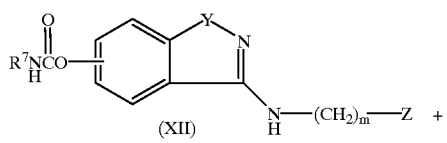
(XII)

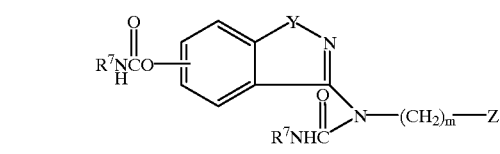
(XIII)

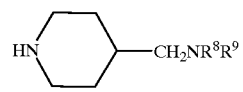
(XVII)

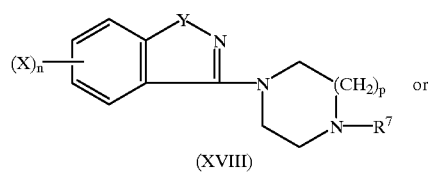
(XVIII)

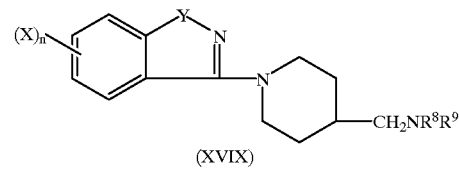
(XVIX)

In the case where $R_1$ and $R_2$ together form a ring, the chloro compound of Formula III when X is alkoxy is reacted with the cyclic amino compound of Formula XVI or XVII to yield the compound of Formula XVIII or XVIX respectively as shown in Reaction Scheme C. The reaction is typically carried out neat in a sealed tube at a temperature of from about 100° C. to about 200° C., preferably from about 120° C. to about 180° C., most preferably from about 130° C. to about 150° C. for from about 1.0 hour to about 100 hours, preferably from about 1 hour to about 72 hours, most preferably from about 2 hours to about 48 hours.

In the case where $R^7$ is hydrogen, the compound of Formula XVIII can then be reacted with the appropriate halo compound, optionally in the presence of a base such as triethylamine or sodium bicarbonate to obtain the desired compounds where $R^7$, $R^8$ and $R^9$ is not hydrogen. The reaction is typically carried out either reactor in an organic solvent such as for example methylene chloride, dimethylformamide or ethanol. Alternatively, $R^7$, $R^8$ and $R^9$ can be other than hydrogen in the first step depicted in this reaction scheme.

The alkoxy compounds are then reacted as shown in Reaction Scheme A.

REACTION SCHEME C

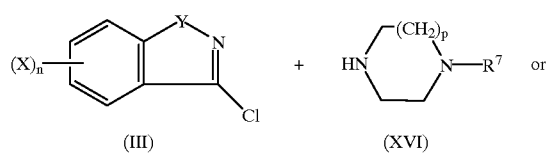

(III)     (XVI)

In the case where X is amino or substituted amino the compounds can be prepared from the corresponding nitro compound which is reduced, by known means, for example, by catalytic reduction. The amino compound is subsequently acylated by means known in the art to provide the amide compounds of the invention. The nitro compounds can be prepared either by nitration of the compound of Formula III or V by means known in the art.

The starting compounds of Formula III are prepared by means known in the art, for example Yevich, J. P. et al., J. Med Chem., 29, 359–69 (1986).

The starting compound of Formula VIII are prepared from the corresponding orthofluorobenzonitriles or orthonitrobenzonitriles as shown in Reaction Scheme D.

More particularly the benzonitrile of Formula XIV where Q is fluoro or nitro and X is as stated above or nitro is reacted with acetohydroxamic acid in an inert polar solvent such as, for example DMF in the presence of a base such as, for example, potassium tertiary butoxide, to obtain the amino compound of Formula VIII directly. Alternatively, the benzonitrile of Formula XIV is reacted with acetone oxime in the presence of a base such as, for example, sodium hydride, to yield the corresponding methylethylideneaminoxybenzonitrile of Formula XV. The compound of Formula XV is subsequently cyclized to the corresponding amino compound of Formula VIII by treatment with acid such as, for example, hydrochloric acid.

REACTION SCHEME D

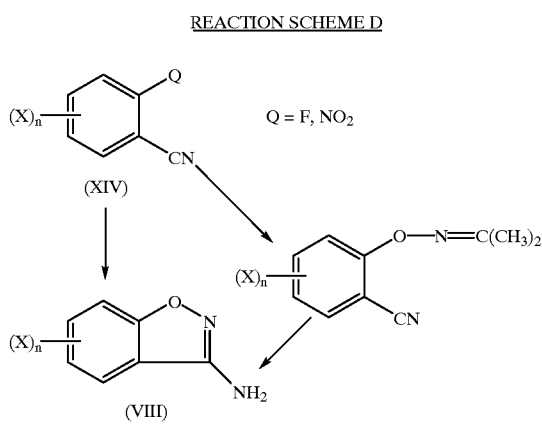

The starting compounds of Formula III or VIII where X is alkoxy are brominated by means known in the art to obtain the corresponding brominated compound.

More particularly, as shown in Reaction Scheme E, the compound of Formula III is brominated in an acid such as for example, acetic acid, at about ambient temperature and the compound of Formula XVI is brominated in a solvent such as for example, methanol at low temperature, preferably, at about $-50°$ C.

REACTION SCHEME E

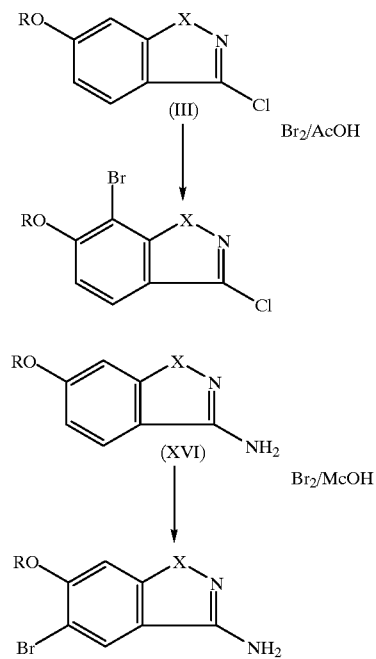

The compounds of the present invention are useful for the treatment of various memory dysfunctions characterized by a decreased cholinergic function such as Alzheimer's disease. Compounds of this invention also inhibit monoamine oxidase and hence are useful as antidepressants.

Cholinesterase Inhibition Assay

Cholinesterases are found through the body, both in the brain and in serum. However, only brain acetylcholinesterase (AChE) distribution is correlated with central cholinergix innervation. This same innervation is suggested to be weakened in Alzheimer patients. We have determined in vitro inhibition of acetylcholinesterase activity in rat striatum.

In Vitro Inhibition of Acetylcholinesterase Activity in Rat Striatum

Acetylcholinesterase (AChE), which is sometimes called true or specific cholinesterase, is found in nerve cells, skeletal muscle, smooth muscle, various glands and red blood cells. AChE may be distinguished from other cholinesterases by substrate and inhibitor specificities and by regional distribution. Its distribution in brain roughly correlates with cholinergic innervation and subfractionation shows the highest level in nerve terminals.

It is generally accepted that the physiological role of AChE is the rapid hydrolysis and inactivation of acetylcholine. Inhibitors of AChE show marked cholinomimetic effects in cholinergically-innervated effector organs and have been used therapeutically in the treatment of glaucoma, myasthenia gravis and paralytic ileus. However, recent studies have suggested that AChE inhibitors may also be beneficial in the treatment of Alzheimer's disease.

The method described below was used in this invention for assaying cholinesterase activity. This is a modification of the method of Ellman et al., Biochem. Pharmacol. 7, 88 (1961).

Procedure

A. Reagents
1. 0.05M Phosphate buffer, pH 7.2
   (a) 6.85 g $NaH_2PO_4.H_2O$/100 ml distilled $H_2O$
   (b) 13.40 g $Na_2HPO_4.7H_2O$/100 ml distilled $H_2O$
   (c) add (a) to (b) until pH reaches 7.2
   (d) Dilute 1:10
2. Substrate in buffer
   (a) 198 mg acetylthiocholine chloride (10 mM)
   (b) bring to 100 ml with 0.05M phosphate buffer, pH 7.2 (reagent 1)
3. DTNB in buffer
   (a) 19.8 mg 5,5-dithiobisnitrobenzoic acid (DTNB) (0.5 mM)
   (b) bring to 100 ml with 0.05M phosphate buffer, pH 7.2 (reagent 1)
4. A 2 mM stock solution of the test drug is made up in a suitable solvent and brought to volume with 0.5 mM DTNB (reagent 3). Drugs are serially diluted (1:10) such that the final concentration (in cuvette) is $10^{-4}M$ and screened for activity. If active, $IC_{50}$ values are determined from the inhibitor activity of subsequent concentrations.

B. Tissue Preparation

Male Wistar rats are decapitated, brains rapidly removed, corpora striata dissected free, weighed and homogenized in 19 volumes (approximately 7 mg protein/ml) of 0.05M phosphate buffer, pH 7.2 using a Potter-Elvehjem homogenizer. A 25 microliter aliquote of the homogenate is added to 1.0 milliter vehicle or various concentrations of the test drug and preincubated for 10 minutes at 37° C.

C. Assay

Enzyme activity is measured with the Beckman DU-50 spectrophotometer. This method can be used for $IC_{50}$ determinations and for measuring kinetic constants.

Instrument Settings

Kinetics Soft-Pac Module #598273 (10)

Program #6 Kindata:

Source—Vis

Wavelength—412 nm

Sipper—none

Cuvettes—2 ml cuvettes using auto 6-sampler
Blank—1 for each substrate concentration
Interval time—15 seconds (15 or 30 seconds for kinetics)
Total time—5 minutes (5 or 10 minutes for kinetics)
Plot—yes
Span—autoscale
Slope—increasing
Results—yes (gives slope)
Factor—1

Reagents are added to the blank and sample cuvettes as follows:

Blank
    0.8 ml Phosphate Buffer/DTNB
    0.8 ml Buffer/Substrate

Control
    0.8 ml Phosphate Buffer/DTNB/Enzyme
    0.8 ml Phosphate Buffer/Substrate Drug
    0.8 ml Phosphate Buffer/DTNB/Drug/Enzyme
    0.8 ml Phosphate Buffer/Substrate Blank values are determined for each run to control for non-enzymatic hydrolysis of substrate and these values are automatically subtracted by the kindata program available on kinetics soft-pac module. This program also calculates the rate of absorbance change for each cuvette.

For $IC_{50}$ Determinations

Substrate concentration is 10 mM diluted 1:2 in assay yielding final concentration of 5 mM. DTNB concentration is 0.5 mM yielding 0.25 mM final concentration.

$$\% \text{ Inhibition} = \frac{\text{slope control} - \text{slope drug}}{\text{slope control}} \times 100$$

$IC_{50}$ values are calculated from log-probit analysis

Results of this assay for some of the compounds of this invention and physostigmine (reference compound) are presented in Table 1.

TABLE I

| Compound | Inhibitory Concentration, $IC_{50}$ (µM) Brain AChE |
|---|---|
| 3-[N-methyl, N-2-(4-morpholinyl)ethyl] amino-1,2-benzisoxazol-6-yl methyl carbamate | 13 |
| 7-Bromo-3-[N-methyl, N-2-(4-morpholinyl)-ethyl]amino-1,2-benzisoxazole-6-yl dimethylcarbamate | 2.0 |
| 6-Methoxy-N-methyl-N-[2-[4-(1-phenylmethyl)piperdinyl]ethyl]-1,2-benzisoxazol-3-amine sesquihydrochloride | 4.0 |
| 3-[1-(4-Pyridyl)piperazinyl]-1,2-benzisoxazol-6-yl dimethylcarbamate | 0.88 |
| 7-Bromo-6-methoxy-3-[1-(4-pyridyl)-piperazinyl]-1,2-benzisoxazole (Reference Compound) | 14 |
| Physostigmine | 0.034 |

The utility is further demonstrated by the ability of these compounds to inhibit the enzyme monoamine oxidase, increase the brain levels of biogenic amine(s), and act as antidepressants.

Inhibition of Type A and Type B Monoamine Oxidase Activity in Rat Brain Synaptosomes Purpose To determine the selective inhibition of the two forms of monoamine oxidase (MAO).

Introduction

The metabolic deamination of amines has been known for over a hundred years, but more recently Johnston 1) described two forms of monoamine oxidase, which are called "type A" and "type B". The existence of the two forms is based on different substrate and inhibitor specificities. Serotonin (5HT) and norepinephrine (NE) are substrates for type A MAO, β-phenethylamine (PEA) and benzylamine are substrates for type B MAO, while dopamine (DA) and tyramine are substrates for both types. Clorgyline is a selective inhibitor of the type A enzyme, deprenyl and pargyline are selective inhibitors of the type B enzyme and tranylcypromine and iproniazid are nonselective inhibitors (2). It is recognized that MAO inhibitors have antidepressant properties.

Although various methods for measuring MAO activity are available, the described method involves the extraction of the radiolabeled deaminated metabolites of [$^3$H]-5HT or [$^{14}$C]-β-phenethylamine. This procedure allows MAO-A and MAO-B activities to be measured either simultaneously or individually (3).

Procedure

A. Reagents

1. Phosphate buffer (0.5M), pH 7.4
   134.4 g $NaH_2PO_4 \cdot 7H_2O$, bring to 1 liter in distilled $H_2O$ (A)
   17.3 g $Na_2HPO_4$, bring to 250 ml in distilled $H_2O$ (B)
   Adjust pH of A to 7.4 by slowly adding B (volumes as needed)
   Dilute 1:10 in distilled $H_2O$ (0.05M $PO_4$ buffer, pH 7.4)

2. 0.25M Sucrose ($PO_4$ buffered)
   21.4 g sucrose, bring to 250 ml with 0.05M $PO_4$ buffer 3. Substrate for MAO-A
   a. Serotonin creatinine $SO_4$ (5HT) is obtained from Sigma Chemical Company.
   A 5 mM stock solution is made up in 0.01N HCl. This is used to dilute the specific activity of the [$^3$H]-5HT.
   b. [$^3$H]-5-Hydroxytryptamine creatinine $SO_4$ (20–30 Ci/mmol) is obtained from New England Nuclear.
   c. Add 12 µl of [$^3$H]-5HT to 2 ml of the 5 mM 5HT solution. (Final amine concentration in the assay is 200 µM: see below.)

4. Substrate for MAO-B
   a. β-phenethylamine (PEA) is obtained form Sigma Chemical Company. A 5 mM stock solution is made up in 0.01N HCl. This is used to dilute the specific activity of the [$^{14}$C]-PEA.
   b. β-[ethyl-1-$^{14}$C]-phenethylamine hydrochloride (40–50 mCi/mmol) is obtained from New England Nuclear.
   c. Add 12 µl of [$^{14}$C]-PEA to 2 ml of the 5 mM PEA solution. (final amine concentration in the assay is 200 µM: see below.)

5. Equal amounts of MAO-A (5HT) and MAO-B (PEA) substrates are combined for simultaneously testing both MAO types, i.e. mixed stock solution of 2.5 mM 5HT and 2.5 mM PEA, 40 µl of this mixed solution gives a 200 µM final concentration of each amine in the assay. When testing only one MAO type, the individual 5 mM stock solutions must be diluted 1:1 with distilled water prior to adding 40 µl to the incubation mixture; i.e., same 200 µM final amine concentration.

B. Tissue Preparation

Male Wistar rats weighing 150–250 grams were sacrificed and the brains rapidly removed. Whole brain minus cerebellum was homogenized in 30 volumes of ice-cold, phosphate-buffered 0.25M sucrose, using a Potter-Elvehjem homogenizer. The homogenate was centrifuged at 1000 g for 10 minutes and the supernatant ($S_1$) decanted and recentrifuged at 18,000 g for 20 minutes. The resulting pellet ($P_2$) was resuspended in fresh 0.25M sucrose and served as the tissue source for mitochondrial MAO.

C. Assay

10 µl 0.5M $PO_4$ buffer, pH 7.4

50 µl $H_2O$ or appropriate drug concentration

400 µl Tissue suspension

Tubes are preincubated for 15 minutes at 37° C. and the assay is started by adding 40 µl of combined substrate ($[^3H]$-5HT and $[^{14}C]$-PEA at 15 second intervals. The tubes are incubated for 30 minutes at 37° C. and the reaction stopped by the addition of 0.3 ml 2N HCl. Tissue blank values are determined by adding the acid before the radioactive substrate. The oxidative products of the reaction are extracted with ethyl acetate/toluene (1:1). 5 ml of this mixture is added to the tubes. The resultant mixture is vortexed for 15 seconds to extract the deaminated metabolites into the organic phase and the latter is allowed to separate from the aqueous phase. The tubes are placed in acetone/dry ice bath to freeze the aqueous layer. When this layer is frozen, the top organic layer is poured into a scintillation vial. 10 ml of Liquiscint is added and the samples are counted using window settings for $^{14}C$ in one channel and $^3H$ in the second channel. $IC_{50}$ values are determined by log-probit analysis.

References

1. Johnston, J. P.: Some observations upon a new inhibitor of monoamine oxidase in brain tissue. Biochem. Pharmacol. 17:1285–1297 (1968).
2. Fowler, C. J. and Ross, S. B.: Selective inhibitors of monoamine oxidase A and B: biochemical, pharmacological and clinical properties. Med. Res. Rev. 4:323–328 (1984).
3. Kindt, M. V., Youngster, S. K., Sonsalla, P. K., Duvoisin, R. C. and Heikkila, R. E.: Rose of monoamine oxidase-A (MOA-A) in the bioactivatin and nigrostriatal dopaminergic neurotoxicity of the MPTP analog, 2 Me-MPTP. Eur. J. Pharmacol. 46:313–318 (1988).

Results of the monoamine oxidase inhibition assay for representative compounds of this invention are presented in Table II.

TABLE II

| Compound | Inhibitory Concentration — $IC_{50}$ (µM) | |
|---|---|---|
| | MAO-A | MAO-B |
| 6-Methoxy-N-methyl-N-[2-(4-morpholinyl)ethyl]-1,2-benzisoxazol-3-amine | 13 | >$10^3$ |
| 6-Methoxy-N-[2-(methyl-amino)ethyl]-1,2-benzisoxazol-3-amine | 25 | |
| 6-Methoxy-3-[1-(4-pyridyl)-piperazinyl]-1,2-benzisoxazole | 10 | 45 |

TABLE II-continued

| Compound | Inhibitory Concentration — $IC_{50}$ (µM) | |
|---|---|---|
| | MAO-A | MAO-B |
| (Reference Compound) | | |
| Brofaromine | 0.18 | 23 |

Ex vivo Monoamine Oxidase Inhibition Assay

The enzyme monoamine oxidase (MAO) exists in two catalytically distinguishable forms termed MAO-A and MAO-B. The ability of the compounds of the invention to inhibit MAO ex vivo in the rat was determined using a procedure adapted from the procedure set forth in *The Journal of Pharmacology and Experimental Therapeutics*, Vol. 248, No. 1, (1989), pp. 400–414.

Procedure

The compound to be tested was administered to male Wistar rats orally. At specified times after administration the rats were decapitated and the whole brain without cerebellum was dissected rapidly and frozen on dry ice. The samples were stored at −80° C. until measurement of the MAO activity. After thawing, the tissues were homogenized in 5 volumes of 0.1 mol/l of potassium-phosphate buffer, pH 7.4, using all glass homogenisers. MAO activity was determined essentially as described by Wurtman and Axelrod. *Biochem. Pharmacol.* 12: 1439–1441, (1963).

The enzyme reaction was started by addition of 80 µl of the MAO-A substrate $[^3H]$-5-HT (0.96 mCi/mmol, final amine concentration is 200 µM or of the MAO-B substrate $[^{14}C]$PEA (0.192 mCi/mmol, final amine concentration is 200 µM and the incubation continued for 10 minutes at 37° C. Then, the reaction was stopped by addition of 200 µl of 2N HCl, and the deaminated metabolites were extracted by vigorous shaking for 10 minutes with 5 ml of diethylether (5-HT-extraction) or n-heptane (PEA-extraction). After centrifugation (1000×g; 30 sec) the water-phase was frozen in dry ice and the organic layer poured into plastic vials containing 5 ml of scintillation cocktail. Finally, the radioactivity was determined in a scintillation spectrometer. Reaction mixtures as described above but lacking the homogenate served as blanks.

The results are presented in Table III.

TABLE III

| Compound | Ex vivo inhibition (%) of monoamine oxidase at 50 mg/kg, p.o. | | |
|---|---|---|---|
| | Type A | Type B | Time (h) |
| 3-[N-methyl, N-2-(morpholinyl)ethyl]amino-1,2-benzisoxazol-6-yl methylcarbamate | 26 | 19 | 0.5 |
| | 29 | 19 | 1.0 |
| | 42 | 28 | 4.0 |
| | 14 | 12 | 24.0 |
| N-2-(4-morpholinyl)ethyl]-1,2-benzisoxazol-3-amine | 88 | 52 | 0.5 |
| | 85 | 45 | 1.0 |
| | 68 | 33 | 4.0 |
| | 3.5 | 0.0 | 24.0 |
| N-Methyl-N-2-(4-morpholinyl)ethyl]-1,2-benzisoxazole-3-amine | 78 | 32 | 0.5 |
| | 66 | 25 | 1.0 |
| | 76 | 36 | 4.0 |
| | 11 | 0 | 24.0 |
| Meclobemide* (Reference Compound) | 62 | 33 | 1.0 |
| | 57 | 37 | 4.0 |
| | 14 | 9 | 24.0 |

*administered at 10 mg/kg.

Effective quantities of the compounds of the invention may be administered to a patient by any of the various methods, for example, orally as in capsule or tablets, parenterally in the form of sterile solutions or suspensions, and in some cases intravenously in the form of sterile solutions. The free base final products, while effective themselves, may be formulated and administered in the from of their pharmaceutically acceptable acid addition salts for purposes of stability, convenience of crystallization, increased solubility and the like.

Acids useful for preparing the pharmaceutically acceptable acid addition salts of the invention include inorganic acids such as hydrochloric, hydrobromic, sulfuric, nitric, phosphoric and perchloric acids, as well as organic acids such as tartaric, citric, acetic, succinic, maleic, fumaric, 2-naphthalenesulfonic and oxalic acids.

The active compounds of the present invention may be orally administered, for example, with an inert diluent or with an edible carrier, or they may be enclosed in gelatin capsules, or they may be compressed into tablets. For the purpose of oral therapeutic administration, the active compounds of the invention may be incorporated with excipients and used in the form of tablets, troches, capsules, elixirs, suspensions, syrups, wafers, chewing gum and the like. These preparations should contain at least 0.5% of active compounds, but may be varied depending upon the particular form and may conveniently be between 4% to about 70% of the weight of the unit. The amount of active compound in such compositions is such that a suitable dosage will be obtained. Preferred compositions and preparations according to the present invention are prepared so that an oral dosage unit form contains between 1.0–300 milligrams of active compound.

The tablets, pills, capsules, troches and the like may also contain the following ingredients: a binder such as microcrystalline cellulose, gum tragacanth or gelatin; and excipient such as starch or lactose, a disintegrating agent such as alginic acid, Primogel, cornstarch and the like; a lubricant such as magnesium stearate or Sterotex; a glidant such as colloidal silicon dioxide; and a sweetening agent such as sucrose or saccharin may be added or a flavoring agent such as peppermint, methyl salicylate, or orange flavoring. When the dosage unit form is a capsule, it may contain, in addition to materials of the above type, a liquid carrier such as a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the active compounds, sucrose as a sweetening agent and certain preservatives, dyes, coloring and flavors. Materials used in preparing these various compositions should be pharmaceutically pure and non-toxic in the amounts used.

For the purpose of parenteral therapeutic administration, the active compounds of the invention may be incorporated into a solution or suspension. These preparations should contain at least 1.0% of active compound, but may be varied between 0.5 and about 30% of the weight thereof. The amount of active compound in such compositions is such that a suitable dosage will be obtained. Preferred compositions and preparations according to the present inventions are prepared so that a parenteral dosage unit contains between 0.5 to 100 milligrams of active compound.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in disposable syringes or multiple dose vials made of glass or plastic.

The following examples will further illustrate this invention but are not intended to limit it in anyway. In Tables IV and V, typical compounds of the present invention are listed. Following Table V, representative illustrative preparations of compounds of the invention are described.

TABLE IV

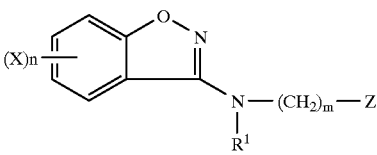

| Ex No | X | $R^1$ | m | Z |
|---|---|---|---|---|
| 1 | 6-OCH$_3$ | CH$_3$ | 2 | 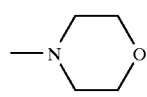 |
| 2 | 6-OH | CH$_3$ | 2 | 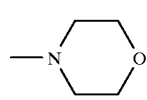 |

TABLE IV-continued
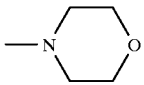
| Ex No | X | R¹ | m | Z |
|---|---|---|---|---|
| 3 | 6-OC(=O)NHCH₃ | CH₃ | 2 | —N(morpholine) |
| 4 | 6-OC(=O)NHCH₂C₆H₅ | CH₃ | 2 | —N(morpholine) |
| 5 | 6-C(=O)NHCH(CH₃)₂ | CH₃ | 2 | —N(morpholine) |
| 6 | H | CH₃ | 2 | —N(morpholine) |
| 7 | H | H | 2 | —N(morpholine) |
| 8 | 6-OCH₃ | H | 2 | —N(morpholine) |
| 9 | 6-OH | H | 2 | —N(morpholine) |
| 10 | 5-OH | H | 2 | —N(morpholine) |
| 11 | 6-OC(=O)NHCH₃ | H | 2 | —N(morpholine) |
| 12 | 5-OC(=O)NHCH₃ | H | 2 | —N(morpholine) |

TABLE IV-continued
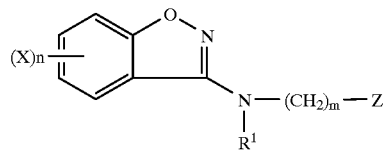
| Ex No | X | R₁ | m | Z |
|---|---|---|---|---|
| 13 | 6-OCH$_2$C$_6$H$_5$ | H | 2 | 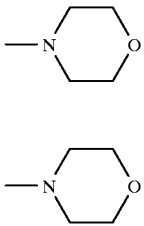 —N(morpholine) |
| 14 | 6-NH$_2$ | H | 2 | —N(morpholine) |
| 15 | 6-NHC(=O)CH$_3$ | H | 2 | —N(morpholine) |
| 16 | 6-Cl | H | 2 | —N(morpholine) |
| 17 | 6-OC(=O)CH$_3$ | H | 2 | —N(morpholine) |
| 18 | 6-OC(=O)N(CH$_3$)$_2$ | H | 2 | —N(morpholine) |
| 19 | 6-OC(=O)CH$_2$C$_6$H$_5$ | H | 2 | —N(morpholine) |
| 20 | 6-OCH$_3$ | CH$_3$ | 2 | —N(piperidine) |
| 21 | 6-OCH$_3$ | CH$_3$ | 3 | —N(morpholine) |
| 22 | 6-OCH$_2$OCH$_3$ | H | 2 | —N(thiomorpholine) |

TABLE IV-continued (X)n-[benzisoxazole]-N(R¹)-(CH₂)ₘ-Z

| Ex No | X | R¹ | m | Z |
|---|---|---|---|---|
| 23 | 6-OH | H | 2 | -N(piperazine)NCH₃ |
| 24 | 6-OCH₃ | H | 2 | -N(CH₃)₂ |
| 25 | 5-OCH₃ | H | 2 | -N(morpholine) |
| 26 | 6-OC(=O)NHCH₃ | C(=O)NHCH₃ | 2 | -N(morpholine) |
| 27 | 5-OC(=O)NHCH₃ | C(=O)NHCH₃ | 2 | -N(morpholine) |
| 28 | 7-Br, 6-OCH₃ | CH₃ | 2 | -N(morpholine) |
| 29 | 5-Br, 6-OCH₃ | H | 2 | -N(morpholine) |
| 30 | 6-OH | H | 2 | -N(thiomorpholine) |
| 31 | 6-OCH₃ | CH₃ | 2 | -(4-methylpiperidine)N-CH₂-phenyl |
| 32 | 7-Br, 6-OH | CH₃ | 2 | -N(morpholine) |
| 33 | 7-Br, 6-OC(=O)N(CH₃)₂ | CH₃ | 2 | -N(morpholine) |

TABLE IV-continued

| Ex No | X | R₁ | m | Z |
|---|---|---|---|---|
| 34 | 6-OCH₃ | CH₃ | 2 | 2-pyridyl |
| 35 | 6-OH | CH₃ | 2 | 2-pyridyl |
| 36 | 6-OC(=O)NHCH₃ | CH₃ | 2 | 2-pyridyl |
| 37 | 6-OC(=O)N(CH₃)₂ | CH₃ | 2 | 2-pyridyl |
| 38 | 6-OC(=O)NHCH(CH₃)₂ | CH₃ | 2 | 2-pyridyl |
| 39 | 6-OC(=O)NHCH₂C₆H₅ | CH₃ | 2 | 2-pyridyl |
| 40 | 6-OC(=O)NH(CH₂)₆CH₃ | CH₃ | 2 | 2-pyridyl |
| 41 | 6-OC(=O)-(1,2,3,4-tetrahydroisoquinolin-2-yl) | CH₃ | 2 | 2-pyridyl |
| 42 | 6-OH | CH₃ | 2 | 1-benzyl-4-piperidyl |
| 43 | 6-OC(=O)NHCH₃ | CH₃ | 2 | 1-benzyl-4-piperidyl |

TABLE IV-continued

[Structure: benzisoxazole with (X)n substituents and N(R¹)-(CH₂)m-Z group]

| Ex No | X | R₁ | m | Z |
|---|---|---|---|---|
| 44 | 6-OC(=O)N(CH₃)₂ | CH₃ | 2 | 4-methyl-piperidine-N-CH₂-phenyl |
| 45 | 6-OC(=O)NHCH(CH₃)₂ | CH₃ | 2 | 4-methyl-piperidine-N-CH₂-phenyl |
| 46 | 6-OC(=O)NHCH₂C₆H₅ | CH₃ | 2 | 4-methyl-piperidine-N-CH₂-phenyl |
| 47 | 6-OC(=O)NH(CH₂)₆CH₃ | CH₃ | 2 | 4-methyl-piperidine-N-CH₂-phenyl |
| 48 | 6-OC(=O)-N(tetrahydroisoquinoline) | CH | 2 | 4-methyl-piperidine-N-CH₂-phenyl |
| 49 | 6-OCH₃ | CH₃ | 2 | piperazine-N-CH₂-phenyl |
| 50 | 6-OH | CH₃ | 2 | piperazine-N-CH₂-phenyl |
| 51 | 6-OC(=O)NHCH₃ | CH₃ | 2 | piperazine-N-CH₂-phenyl |
| 52 | 6-OC(=O)N(CH₃)₂ | CH₃ | 2 | piperazine-N-CH₂-phenyl |
| 53 | 6-OC(=O)NHCH(CH₃)₂ | CH₃ | 2 | piperazine-N-CH₂-phenyl |

TABLE IV-continued

Structure: (X)n-benzisoxazole with N(R¹)-(CH₂)m-Z substituent at 3-position

| Ex No | X | R₁ | m | Z |
|---|---|---|---|---|
| 54 | 6-OC(=O)NHCH₂C₆H₅ | CH₃ | 2 | piperazine-N-CH₂-C₆H₅ |
| 55 | 6-OC(=O)NH(CH₂)₆CH₃ | CH₃ | 2 | piperazine-N-CH₂-C₆H₅ |
| 56 | 6-OC(=O)-N(1,2,3,4-tetrahydroisoquinolin-2-yl) | CH₃ | 2 | piperazine-N-CH₂-C₆H₅ |
| 57 | 6-OCH₃ | H | 2 | —NHCH₃ |
| 58 | 6-OH | H | 2 | —NHCH₃ |
| 59 | 6-OC(=O)NHCH₃ | H | 2 | —NHCH₃ |
| 60 | 6-OC(=O)N(CH₃)₂ | H | 2 | —NHCH₃ |
| 61 | 6-OC(=O)NHCH(CH₃)₂ | H | 2 | —NHCH₃ |
| 62 | 6-OC(=O)NHCH₂C₆H₅ | H | 2 | —NHCH₃ |
| 63 | 6-OC(=O)NH(CH₂)₆CH₃ | H | 2 | —NHCH₃ |
| 64 | 6-OC(=O)-N(1,2,3,4-tetrahydroisoquinolin-2-yl) | H | 2 | —NHCH₃ |

TABLE V

Structure: (X)n-benzisoxazole with Q substituent at 3-position

| Ex No | X | Q |
|---|---|---|
| 65 | 6-OCH₃ | piperazin-1-yl (—N(piperazine)NH) |
| 66 | 6-OH | piperazin-1-yl |
| 67 | 6-OC(=O)NHCH₃ | piperazin-1-yl |

TABLE V-continued

[Structure: benzisoxazole with (X)n substituent on benzene ring and Q at 3-position]

| Ex No | X | Q |
|---|---|---|
| 68 | 6-OC(=O)N(CH$_3$)$_2$ | —N(piperazine)NH |
| 69 | 6-OC(=O)NHCH(CH$_3$)$_2$ | —N(piperazine)NH |
| 70 | 6-OC(=O)NHCH$_2$C$_6$H$_5$ | —N(piperazine)NH |
| 71 | 6-OC(=O)NH(CH$_2$)$_6$CH$_3$ | —N(piperazine)NH |
| 72 | 6-OC(=O)—N(1,2,3,4-tetrahydroisoquinolin-2-yl) | —N(piperazine)NH |
| 73 | 6-OCH$_3$ | —N(piperidine)CH$_2$NH$_2$ |
| 74 | 6-OH | —N(piperidine)CH$_2$NH$_2$ |
| 75 | 6-OC(=O)NHCH$_3$ | —N(piperidine)CH$_2$NH$_2$ |
| 76 | 6-OC(=O)N(CH$_3$)$_2$ | —N(piperidine)CH$_2$NH$_2$ |
| 77 | 6-OC(=O)NHCH(CH$_3$)$_2$ | —N(piperidine)CH$_2$NH$_2$ |
| 78 | 6-OC(=O)NHCH$_2$C$_6$H$_5$ | —N(piperidine)CH$_2$NH$_2$ |

TABLE V-continued

[Structure: benzisoxazole core with (X)ₙ substituent on benzene ring and Q substituent at 3-position]

| Ex No | X | Q |
|---|---|---|
| 79 | 6-OC(=O)NH(CH₂)₆CH₃ | N-methylpiperidin-4-yl-CH₂NH₂ |
| 80 | 6-OC(=O)-N(1,2,3,4-tetrahydroisoquinolin-2-yl) | N-methylpiperidin-4-yl-CH₂NH₂ |
| 81 | 6-OCH₃ | N-methylpiperidin-4-yl-CH₂N(CH₂C₆H₅)₂ |
| 82 | 6-OH | N-methylpiperidin-4-yl-CH₂N(CH₂C₆H₅)₂ |
| 83 | 6-OC(=O)NHCH₃ | N-methylpiperidin-4-yl-CH₂N(CH₂C₆H₅)₂ |
| 84 | 6-OC(=O)N(CH₃)₂ | N-methylpiperidin-4-yl-CH₂N(CH₂C₆H₅)₂ |
| 85 | 6-OC(=O)NHCH(CH₃)₂ | N-methylpiperidin-4-yl-CH₂N(CH₂C₆H₅)₂ |
| 86 | 6-OC(=O)NHCH₂C₆H₅ | N-methylpiperidin-4-yl-CH₂N(CH₂C₆H₅)₂ |
| 87 | 6-OC(=O)NH(CH₂)₆CH₃ | N-methylpiperidin-4-yl-CH₂N(CH₂C₆H₅)₂ |
| 88 | 6-OC(=O)-N(1,2,3,4-tetrahydroisoquinolin-2-yl) | N-methylpiperidin-4-yl-CH₂N(CH₂C₆H₅)₂ |
| 89 | 6-OCH₃ | 4-methylpiperazin-1-yl-CH₂C=CH |

TABLE V-continued
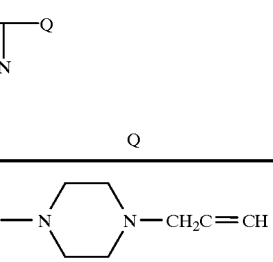
| Ex No | X | Q |
|---|---|---|
| 90 | 6-OH | 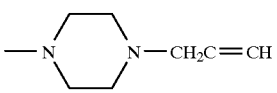 |
| 91 | 6-OC(=O)NHCH$_3$ | 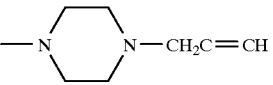 |
| 92 | 6-OC(=O)N(CH$_3$)$_2$ | 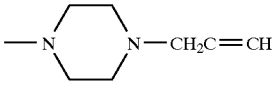 |
| 93 | 6-OC(=O)NHCH(CH$_3$)$_2$ | 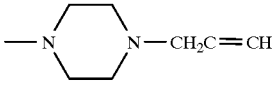 |
| 94 | 6-OC(=O)NHCH$_2$C$_6$H$_5$ | 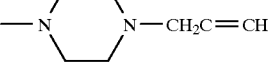 |
| 95 | 6-OC(=O)NH(CH$_2$)$_6$CH$_3$ | 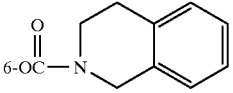 |
| 96 | 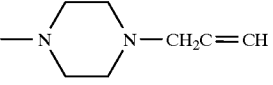 | 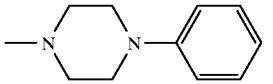 |
| 97 | 6-OCH$_3$ | 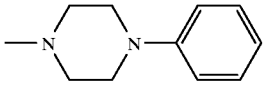 |
| 98 | 6-OH | 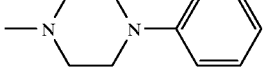 |
| 99 | 6-OC(=O)NHCH$_3$ | 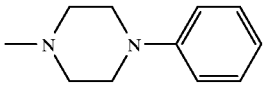 |
| 100 | 6-OC(=O)N(CH$_3$)$_2$ | |

TABLE V-continued

| Ex No | X | Q |
|---|---|---|
| 101 | 6-OC(=O)NHCH(CH₃)₂ | —N(piperazine)N-phenyl |
| 102 | 6-OC(=O)NHCH₂C₆H₅ | —N(piperazine)N-phenyl |
| 103 | 6-OC(=O)NH(CH₂)₆CH₃ | —N(piperazine)N-phenyl |
| 104 | 6-OC(=O)-(tetrahydroisoquinolin-2-yl) | —N(piperazine)N-phenyl |
| 105 | 6-OCH₃ | —N(piperazine)N-(4-pyridyl) |
| 106 | 6-OH | —N(piperazine)N-(4-pyridyl) |
| 107 | 6-OC(=O)NHCH₃ | —N(piperazine)N-(4-pyridyl) |
| 108 | 6-OC(=O)N(CH₃)₂ | —N(piperazine)N-(4-pyridyl) |
| 109 | 6-OC(=O)NHCH(CH₃)₂ | —N(piperazine)N-(4-pyridyl) |
| 110 | 6-OC(=O)NHCH₂C₆H₅ | —N(piperazine)N-(4-pyridyl) |
| 111 | 6-OC(=O)NH(CH₂)₆CH₃ | —N(piperazine)N-(4-pyridyl) |

TABLE V-continued

| Ex No | X | Q |
|---|---|---|
| 112 | 6-OC(=O)-N(tetrahydroisoquinoline) | -N(piperazine)N-(4-pyridyl) |
| 113 | 6-OCH₃ | -N(piperazine)N-(2-pyridyl) |
| 114 | 6-OH | -N(piperazine)N-(2-pyridyl) |
| 115 | 6-OC(=O)NHCH₃ | -N(piperazine)N-(2-pyridyl) |
| 116 | 6-OC(=O)N(CH₃)₂ | -N(piperazine)N-(2-pyridyl) |
| 117 | 6-OC(=O)NHCH(CH₃)₂ | -N(piperazine)N-(2-pyridyl) |
| 118 | 6-OC(=O)NHCH₂C₆H₅ | -N(piperazine)N-(2-pyridyl) |
| 119 | 6-OC(=O)NH(CH₂)₆CH₃ | -N(piperazine)N-(2-pyridyl) |
| 120 | 6-OC(=O)-N(tetrahydroisoquinoline) | -N(piperazine)N-(2-pyridyl) |
| 121 | 6-OCH₃ | -N(piperazine)N-(6-chloropyrimidin-4-yl) |

TABLE V-continued
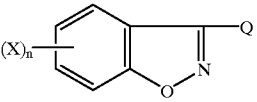
| Ex No | X | Q |
|---|---|---|
| 122 | 6-OH | 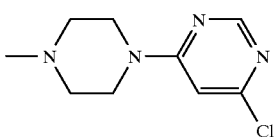 |
| 123 | 6-OC(=O)NHCH$_3$ | 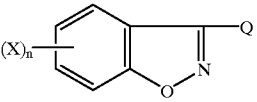 |
| 124 | 6-OC(=O)N(CH$_3$)$_2$ | 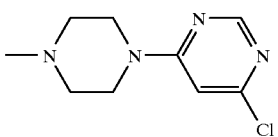 |
| 125 | 6-OC(=O)NHCH(CH$_3$)$_2$ | 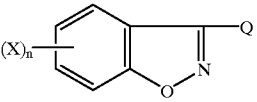 |
| 126 | 6-OC(=O)NHCH$_2$C$_6$H$_5$ | 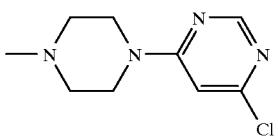 |
| 127 | 6-OC(=O)NH(CH$_2$)$_6$CH$_3$ | 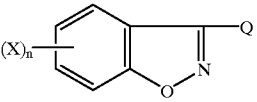 |
| 128 | 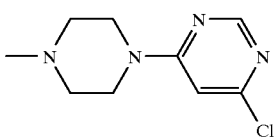 | 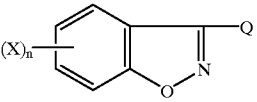 |
| 129 | 6-OCH$_3$ | 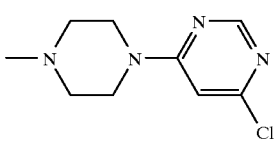 |

TABLE V-continued
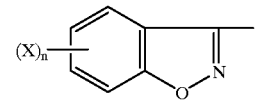
| Ex No | X | Q |
|---|---|---|
| 130 | 6-OH | 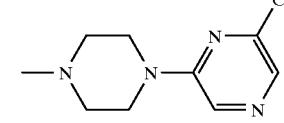 |
| 131 | 6-OC(=O)NHCH₃ | 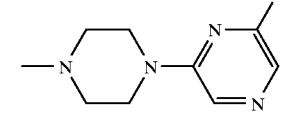 |
| 132 | 6-OC(=O)N(CH₃)₂ | 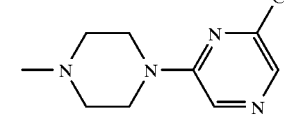 |
| 133 | 6-OC(=O)NHCH(CH₃)₂ | 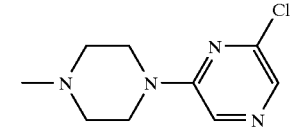 |
| 134 | 6-OC(=O)NHCH₂C₆H₅ | 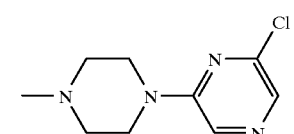 |
| 134 | 6-OC(=O)NH(CH₂)₆CH₃ | 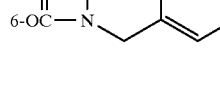 |
| 136 | 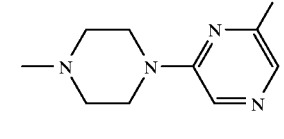 | 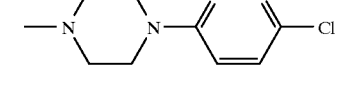 |
| 137 | 6-OCH₃ | 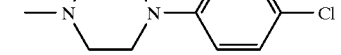 |
| 138 | 6-OH | |

TABLE V-continued
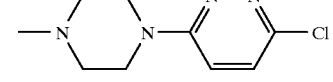
| Ex No | X | Q |
|---|---|---|
| 139 | 6-OC(=O)NHCH₃ | 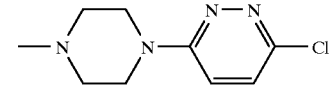 |
| 140 | 6-OC(=O)N(CH₃)₂ | 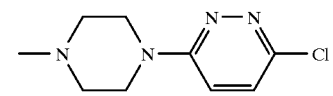 |
| 141 | 6-OC(=O)NHCH(CH₃)₂ | 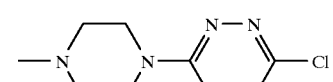 |
| 142 | 6-OC(=O)NHCH₂C₆H₅ | 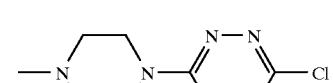 |
| 143 | 6-OC(=O)NH(CH₂)₆CH₃ | 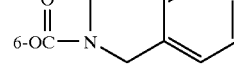 |
| 144 | 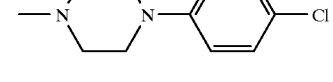 | 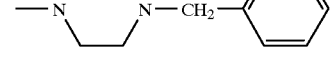 |
| 145 | 6-OCH₃ | 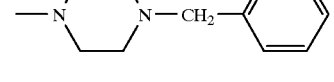 |
| 146 | 6-OH | 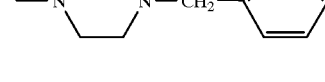 |
| 147 | 6-OC(=O)NHCH₃ | 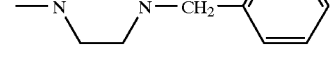 |
| 148 | 6-OC(=O)N(CH₃)₂ | 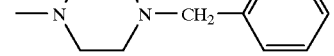 |
| 149 | 6-OC(=O)NHCH(CH₃)₂ | |

TABLE V-continued

[Structure: benzisoxazole with (X)ₙ substituent on benzene ring and Q at 3-position]

| Ex No | X | Q |
|---|---|---|
| 150 | 6-OC(=O)NHCH₂C₆H₅ | —N(piperazine)N—CH₂—C₆H₅ |
| 151 | 6-OC(=O)NH(CH₂)₆CH₃ | —N(piperazine)N—CH₂—C₆H₅ |
| 152 | 6-OC(=O)–N(tetrahydroisoquinoline) | —N(piperazine)N—CH₂—C₆H₅ |
| 153 | 6-OCH₃ | —N(piperazine)N—CH₂—(3-CH₃-C₆H₄) |
| 154 | 6-OH | —N(piperazine)N—CH₂—(3-CH₃-C₆H₄) |
| 155 | 6-OC(=O)NHCH₃ | —N(piperazine)N—CH₂—(3-CH₃-C₆H₄) |
| 156 | 6-OC(=O)N(CH₃)₂ | —N(piperazine)N—CH₂—(3-CH₃-C₆H₄) |
| 157 | 6-OC(=O)NHCH(CH₃)₂ | —N(piperazine)N—CH₂—(3-CH₃-C₆H₄) |
| 158 | 6-OC(=O)NHCH₂C₆H₅ | —N(piperazine)N—CH₂—(3-CH₃-C₆H₄) |

TABLE V-continued

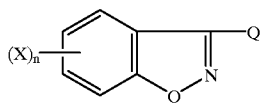

| Ex No | X | Q |
|---|---|---|
| 159 | 6-OC(=O)NH(CH$_2$)$_6$CH$_3$ | N-methylpiperazine-CH$_2$-(3-methylphenyl) |
| 160 | 6-OC(=O)-(1,2,3,4-tetrahydroisoquinolin-2-yl) | N-methylpiperazine-CH$_2$-(3-methylphenyl) |
| 161 | 6-OCH$_3$ | 4-(N-methylpiperazinyl)quinoline |
| 162 | 6-OH | 4-(N-methylpiperazinyl)quinoline |
| 163 | 6-OC(=O)NHCH$_3$ | 4-(N-methylpiperazinyl)quinoline |
| 164 | 6-OC(=O)N(CH$_3$)$_2$ | 4-(N-methylpiperazinyl)quinoline |
| 165 | 6-OC(=O)NHCH(CH$_3$)$_2$ | 4-(N-methylpiperazinyl)quinoline |

TABLE V-continued
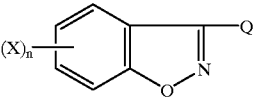
| Ex No | X | Q |
|---|---|---|
| 166 | 6-OC(=O)NHCH$_2$C$_6$H$_5$ | 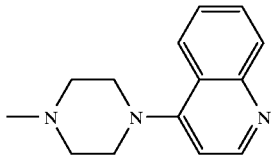 |
| 167 | 6-OC(=O)NH(CH$_2$)$_6$CH$_3$ | 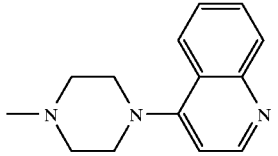 |
| 168 | 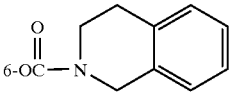 | 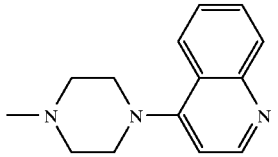 |
| 169 | 6-OCH$_3$ | 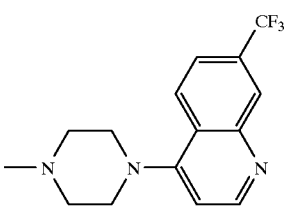 |
| 170 | 6-OH | 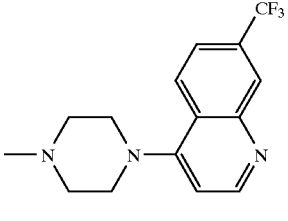 |
| 171 | 6-OC(=O)NHCH$_3$ | 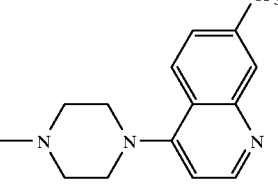 |

TABLE V-continued

[Structure: benzisoxazole with (X)n substituent and Q at 3-position]

| Ex No | X | Q |
|---|---|---|
| 172 | 6-OC(=O)N(CH₃)₂ | 4-(4-methylpiperazin-1-yl)-7-(trifluoromethyl)quinoline |
| 173 | 6-OC(=O)NHCH(CH₃)₂ | 4-(4-methylpiperazin-1-yl)-7-(trifluoromethyl)quinoline |
| 174 | 6-OC(=O)NHCH₂C₆H₅ | 4-(4-methylpiperazin-1-yl)-7-(trifluoromethyl)quinoline |
| 175 | 6-OC(=O)NH(CH₂)₆CH₃ | 4-(4-methylpiperazin-1-yl)-7-(trifluoromethyl)quinoline |
| 176 | 6-OC(=O)-N(3,4-dihydroisoquinolin-2(1H)-yl) | 4-(4-methylpiperazin-1-yl)-7-(trifluoromethyl)quinoline |
| 177 | 6-OCH₃ | 7-chloro-4-(4-methylpiperazin-1-yl)quinoline |

TABLE V-continued

| Ex No | X | Q |
|---|---|---|
| 178 | 6-OH | 7-chloro-4-(4-methylpiperazin-1-yl)quinoline |
| 179 | 6-OC(=O)NHCH$_3$ | 7-chloro-4-(4-methylpiperazin-1-yl)quinoline |
| 180 | 6-OC(=O)N(CH$_3$)$_2$ | 7-chloro-4-(4-methylpiperazin-1-yl)quinoline |
| 181 | 6-OC(=O)NHCH(CH$_3$)$_2$ | 7-chloro-4-(4-methylpiperazin-1-yl)quinoline |
| 182 | 6-OC(=O)NHCH$_2$C$_6$H$_5$ | 7-chloro-4-(4-methylpiperazin-1-yl)quinoline |
| 183 | 6-OC(=O)NH(CH$_2$)$_6$CH$_3$ | 7-chloro-4-(4-methylpiperazin-1-yl)quinoline |

TABLE V-continued

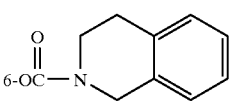

| Ex No | X | Q |
|---|---|---|
| 184 | 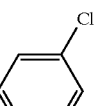 |  |
| 185 | 7-Br, 6-OH | 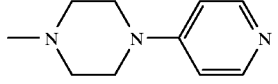 |
| 186 | 7-Br, 6-OCH$_3$ | |

EXAMPLE 1

6-Methoxy-N-methyl-N-[2-(4-morpholinyl)ethyl]-1,2-benzisoxazol-3-amine

To a sealed tube was added 3-chloro-6-methoxy-1,2-benzisoxazole (6.0 g) and N-methyl-N-[2-(4-morpholinyl)ethyl]-amine (13.8 g). The reaction was heated to 140° C. over 48 hours and then cooled to room temperature. The residue was partitioned between ethyl acetate (EtOAc) and water, extracted again with EtOAc, and the organic phase was dried over magnesium sulfate (MgSO$_4$) and concentration in vacuo. Flash column chromatography (silica gel) eluting with 1% methanol/dichloromethane (MeOH/DCM) provided the product (4.7 g), m.p. 43–44° C.

ANALYSIS

Calculated for C$_{15}$H$_{21}$N$_3$O$_3$: 61.84% C 7.26% H 14.42% N Found: 61.75% C 6.98% H 14.46% N

EXAMPLE 2

3-[[2-(4-Morpholinyl)ethyl]methylamino]-1,2-benzisoxazol-6-ol

6-Methoxy-N-methyl-N-[2-(4-morpholinyl)ethyl]-1,2-benzisoxazol-3-amine (7.0 g) was dissolved in 48% hydrobromic acid (130 ml) and heated to reflux under nitrogen for 3 hours. The reaction was cooled to room temperature, neutralized with saturated sodium carbonate (Na$_2$CO$_3$) extracted with ethyl acetate, dried over MgSO$_4$ and concentrated in vacuo. Flash chromatography (silica gel) eluting with 2:1 heptane/acetone provided the product (6.0 g), m.p. 91–92° C.

ANALYSIS

Calculated for C$_{14}$H$_{19}$N$_3$O$_3$: 60.63% C 6.91% H 15.15% N Found: 60.36% C 6.94% H 14.96% N

EXAMPLE 3

3-[[-(4-Morpholinyl)ethyl]methylamino]-1,2-benzisoxazol-6-yl methylcarbamate

To a stirred solution of 3-[[2-(4-morpholinyl)ethyl]methylamino]-1,2-benzisoxazol-6-ol (2 g) and copper(I) chloride (0.3 g) in EtOAc (60 ml) was added methyl isocyanate (0.5 g). After 3.5 hours thin layer chromatography (TLC) (silica gel, 10% MeOH/DCM) showed no starting material. The reaction was filtered through neutral alumina eluting with EtOAc (2 l) and the filtrate was concentrated in vacuo to yield 1.2 g of the product, m.p. 94–95° C.

ANALYSIS

Calculated for C$_{16}$H$_{22}$N$_4$O$_4$: 57.47% C 6.63% H 16.76% N Found: 57.61% C 6.67% H 16.60% N

EXAMPLE 4

3-[[2-(4-Morpholinyl)ethyl]methylamino]-1,2-benzisoxazol-6-yl phenylmethylcarbamate To a stirred solution of 3-[[2-(4-morpholinyl)ethyl]methylamino]-1,2-benzisoxazol-6-ol (2.3 g) and 1,8-diazabicyclo[5.4.0]undec-7-ene (0.2 g) in EtOAc (80 ml) was added phenylmethyl isocyanate (1.3 g). After 24 hours an additional equivalent of the isocyanate was added. TLC (silica gel, 10% MeOH/DCM) showed no starting material. The reaction was concentrated in vacuo. Flash chromatography (silica gel) eluting with 1% MeOH/DCM provided the product (2.4 g), m.p. 106–107° C.

ANALYSIS

Calculated for C$_{22}$H$_{26}$N$_4$O$_4$: 64.38% C 6.38% H 13.65% N Found: 64.34% C 6.34% H 13.55% N

EXAMPLE 5

3-[[2-(4-Morpholinyl)ethyl]methylamino]-1,2-benzisoxazol-6-yl 1-methylethylcarbamate To a stirred solution of 3-[[2-(4-morpholinyl)ethyl]methylamino]-1,2-benzisoxazol-6-ol (2.2 g) and copper(I) chloride (0.1 g) in EtOAc (50 ml) was added 1-methylethylisocyanate (0.8 g). After 24 hours TLC (silica gel, 10% MeOH/DCM) showed no starting material. The reaction was filtered through neutral alumina eluting with EtOAc (3 l) and the filtrate was concentrated in vacuo. The white solid was flash chromatographed on silica gel eluting with 1% MeOH/DCM to yield 1.2 g of the product, m.p. 99–100° C.

ANALYSIS

Calculated for $C_{18}H_{26}N_4O_4$: 59.65% C 7.23% H 15.46% N Found: 59.78% C 6.98% H 15.11% N

EXAMPLE 6

N-methyl-N-[2-(4-morpholinyl)ethyl]-1,2-benzisoxazol-3-amine

To a sealed tube was added 3-chloro-1,2-benzisoxazole (3.0 g) and N-methyl-N-[2-(4-morpholinyl)ethyl]-amine (12.7 g). The reaction was heated to 140° C. over 72 hours and then cooled to room temperature. The residue was partitioned between EtOAc and water, extracted again with EtOAc, and the organic phase was dried over $MgSO_4$ and concentrated in vacuo. Flash column chromatography (silica gel) eluting with 1–3% MeOH/DCM provided the product (1.2 g), as an oil.

ANALYSIS

Calculated for $C_{14}H_{19}N_3O_2$: 64.35% C 7.33% H 16.08% N Found: 64.28% C 7.03% H 15.88% N

EXAMPLE 7

N-[2-(4-Morpholinyl)ethyl]-1,2-benzisoxazol-3-amine

To a solution of 3-amino-1,2-benzisoxazole (3.5 g) in N,N-dimethylformamide (DMF) (100 ml) was added sodium hydride (0.8 g) under nitrogen. The reaction was stirred one hour at ambient temperature. A solution of 4-(2-chloroethyl)morpholine (4.0 g) in DMF (50 ml) was added followed by heating to 120° C. for one hour. TLC (5% MeOH/DCM) analysis revealed the absence of starting material. The reaction was quenched with water and extracted with EtOAc. The organic layer was washed with water, dried ($MgSO_4$), and concentrated in vacuo. Flash column chromatography (silica gel) eluting with 1.5–2.5% MeOH/DCM afforded the product (2.5 g), m.p. 79–80° C.

ANALYSIS

Calculated for $C_{13}H_{17}N_3O_2$: 63.14% C 6.93% H 16.99% N Found: 63.47% C 6.87% H 16.95% N

EXAMPLE 8

6-Methoxy-N-[2-(4-morpholinyl)ethyl]-1,2-benzisoxazol-3-amine a. 3-Amino-6-methoxy-1,2-benzisoxazole

METHOD A

To stirred solution of acetohydroxamic acid (24.6 g) in anhydrous N,N-dimethylformamide (400 ml) was added potassium tertiary butoxide (36.8 g) under nitrogen and stirring was continued for 1 hour. 2-Fluoro-4-methoxy-benzonitrile (33 g) was added to the reaction mixture and stirring was continued for 6 hours. TLC (silica gel) with 10% acetone/chloroform showed no starting material. The reaction was diluted with ethyl acetate (~3 L) and suction filtered. The filtrate was collected and washed with brine (4×1 L), dried ($MgSO_4$) and concentrated in vacuo. The resulting solid was recrystallized from dichloromethane/petroleum ether affording 20 g of product.

Alternatively, 4-methoxy-2-nitro-benzonitrile can be substituted for 2-fluoro-4-methoxy benzonitrile to obtain the same product.

METHOD B

In 20 ml of DMF was dissolved acetone oxime (0.74 g), followed by sodium hydride (0.30 g). After this mixture had stirred for 30 minutes, 4-methoxy-2-nitro-benzonitrile (1.50 g) was added. After an additional 30 minutes the reaction was poured into water (500 ml) and filtered. The solid was collected and dissolved in DCM (250 ml), dried ($MgSO_4$), and concentrated in vacuo. The resulting solid was recrystallized from ethanol to yield 1.5 g of 4-methoxy-2-[[(1-methylethylidene)-amino]oxy]benzonitrile, m.p. 78–79° C.

ANALYSIS

Calculated for $C_{11}H_{12}N_2O_2$: 64.69% C 5.92% H 13.72% N Found: 64.51% C 5.77% H 13.49% N Alternatively, 2-fluoro-4-methoxy-benzonitrile can be substituted for 4-methoxy-2-nitrobenzonitrile.

3-Amino-6-methoxy-1,2-benzisoxazole is prepared following substantially the procedure of Example 25a starting from 4-methoxy-2-[[(1-methylethylidene)amine]-oxy]-benzonitrile.

4-Methoxy-2-[[(1-methylethylidene)amino]benzonitrile

In 20 ml of dry N,N-dimethylformamide was dissolved acetone oxime (0.74 g) followed by sodium hydride (0.30 g). After this mixture has stirred for 30 minutes, 4-methoxy-2-nitro-benzonitrile (1.50 g) was added. After an additional 30 minutes the reaction was poured into water (500 ml) and filtered. The solid was collected and dissolved in dichloromethane (250 ml), dried ($MgSO_4$), and concentrated in vacuo. The resulting solid was recrystallized from ethanol. The product (1.5 g), m.p. 141–142° C.

ANALYSIS

Calculated for $C_{11}H_{12}N_2O_2$: 64.69% C 5.92% H 13.72% N Found: 64.51% C 5.77% H 13.49% N b. 6-Methoxy-N-[2-(4-morpholinyl)ethyl]-1,2benzisoxazol-3amine To a solution of 3-amino-6-methoxy-1,2-benzisoxazole (5.5 g) in N,N-dimethylformamide (DMF) (100 ml) was added sodium hydride (1.2 g) under nitrogen. The reaction was stirred one hour at ambient temperature. A solution of 4-(2-chloroethyl)morpholine (5.4 g) in DMF (50 ml) was added to the reaction and heated to 125° C. for one hour. TLC (5% MeOH/DCM) revealed the absence of starting material. The reaction was quenched with water (1 l) and extracted with EtOAc (2 l). The organic layer was washed with water, dried ($MgSO_4$), and concentrated in vacuo. Flash column chromatography (silica gel) eluting with 3–4% MeOH/DCM afforded the product (4.5 g), m.p. 85–86° C.

ANALYSIS

Calculated for $C_{14}H_{19}N_3O_3$: 60.63% C 6.91% H 15.15% N Found: 60.55% C 6.97% H 15.28% N

EXAMPLE 9

3-[[2-(4-Morpholinyl)ethyl]amino]-1,2-benzisoxazol-6-ol

6-Methoxy-N-[2-(4-morpholinyl)ethyl]-1,2-benzisoxazol-3-amine (2.9 g) was dissolved in 48% hydrobromic acid (50 ml) and heated to reflux under nitrogen for 3 hours. The reaction was cooled to room temperature, neutralized with saturated sodium carbonate ($Na_2CO_3$) solution, and extracted with EtOAc. The organic phase was dried over $MgSO_4$ and concentrated in vacuo. Flash chromatography (silica gel) eluting with 3:2 acetone/heptane and subsequently titration with DCM/heptane provided the product (1.0 g), m.p. 151–152° C.

ANALYSIS

Calculated for $C_{13}H_{17}N_3O_3$: 59.30% C 6.51% H 15.96% N Found: 58.97% C 6.56% H 15.95% N

EXAMPLE 10

3-[[2-(4-Morpholinyl)ethyl]methylamino]-1,2-benzisoxazol-5-ol

5-Methoxy-N-methyl-N-[2-4-morpholinyl)ethyl]-1,2-benzisoxazol-3-amine (2.6 g) was dissolved in 48% hydrobromic acid (40 ml) and heated to reflux under nitrogen for 6 hours. The reaction was cooled to room temperature, neutralized with saturated $Na_2CO_3$ solution, and extracted with EtOAc. The organic phase was dried over $MgSO_4$ and concentrated in vacuo. Flash chromatography (silica gel) eluting with 1:1:20 acetone/MeOH/DCM provided the pure product (2.1 g), 153–154° C.

ANALYSIS

Calculated for $C_{13}H_{17}N_3O_3$: 59.30% 6.51% H 15.96% N Found: 59.00% C 6.50% H 15.78% N

EXAMPLE 11

3-[[2-(4-Morpholinyl)ethyl]amino]-1,2-benzisoxazol-6-yl methylcarbamate

To a stirred solution of 3-[[2-(4-morpholinyl)ethyl]amino]-1,2-benzisoazol-6-ol (2 g) and copper(I)chloride (0.3 g) in EtOAc (60 ml) was added methyl isocyanate (0.5 g). After 3.5 hours TLC (silica gel, 10% MeOH/DCM) showed no starting material. The reaction was filtered through neutral alumina eluting with EtOAc (2 l) and the filtrate was concentrated in vacuo. Flash column chromatography (silica gel) eluting with 1:1:20 acetone/MeOH/DCM afforded a white solid which was recrystallized from EtOAc/pet. ether to yield 0.7 g of the expected product, m.p. 127–128° C.

ANALYSIS

Calculated for $C_{15}H_{20}N_4O_4$: 56.24% C 6.29% H 17.49% N Found: 56.25% C 6.32% H 17.55% N

EXAMPLE 12

3-[[2-(4-Morpholinyl)ethyl]amino]-1,2-benzisoxazol-5-yl methylcarbamate

To a stirred solution of 3-[[2-(4-morpholinyl)ethyl]amino]-1,2-benzisoxazol-5-ol (1 g) and a catalytic amount of copper(I)chloride (0.05 g) in EtOAc (100 ml) was added methyl isocyanate (0.26 g). After 24 hours TLC (silica gel, 1:1:20 acetone/MeOH/DCM) showed no starting material. The reaction was filtered through neutral alumina eluting with EtOAc (1 l) and the filtrate was concentrated in vacuo. The residue was further purified by flash chromatography (silica gel) eluting with 1:1:20 acetone/MeOH/DCM to yield 0.4 g of the product, m.p. 135–136° C.

ANALYSIS

Calculated for $C_{15}H_{20}N_4O_4$: 56.24% C 6.29% H 17.49% N Found: 56.09% C 6.25% H 17.50% N

EXAMPLE 16

6-Chloro-N-[2-(4-morpholinyl)ethyl]-1,2-benzisoxazol-3-amine a. 4-Chloro-2-[[(1-methylethylidene)amino]oxy]benzonitrile In 75 ml of dry N,N-dimethylformamide was dissolved acetone oxime (1.21 g), followed by potassium tertiary butoxide (1.85 g) and stirred under nitrogen. After 30 minutes, 4-chloro-2-nitro-benzonitrile (2.00 g) was added. After an additional 30 minutes the reaction was poured into water (500 ml) and filtered. The solid was collected and dissolved in DCM (250 ml), dried ($MgSO_4$), and concentrated in vacuo. The resulting solid was recrystallized from ethanol to yield 1.5 g of the product, m.p. 83–84° C.

ANALYSIS

Calculated for $C_{10}H_9N_2OCl$: 57.57% C 4.35% H 13.43% N Found: 57.52% C 3.95% H 13.33% N b. 3-Amino-6-chloro-1,2-benzisoxazole 3-Amino-6-chloro-1,2-benzisoxazole is prepared from the product of Example 16a following substantially the procedure of Example 25a.

Alternatively, the same product is obtained from 4-chloro-2-nitrobenzonitrile or 2-fluoro-4-chlorobenzonitrile.

c. 6-Chloro-N-[2-(4-morpholinyl)ethyl]-1,2-benzisoxazol-3-amine

6-Chloro-N-[2,4-morpholinyl)ethyl]-1,2-benzisoxazol-3-amine is prepared from the product of Example 16b following substantially the procedure of Example 8a.

EXAMPLE 18

3-[[2-(4-Morpholinyl)ethyl]amino]-1,2-benzisoxazol-6-yl dimethylcarbamate

To a stirred solution of 3-[[2-(4-morpholinyl(ethyl]amino]-1,2-benzisoxazol-6-ol (Example 9) (1.5 g) and 1,8-diazabicyclo[5.4.0]undec-7-ene (0.13 g) in 1,2-dichloroethane (40 ml) was added dimethylcarbamyl chloride (0.65 g). The mixture was refluxed for 24 hours under $N_2$. TLC (silica gel, 10% MeOH/DCM) showed no starting material. The reaction was filtered and the filtrate concentrated in vacuo. Flash chromatography (silica gel) eluting with 5% acetone/5% MeOH/$CH_2Cl_2$ provided a residue which upon crystallization afforded 0.5 g of the product, m.p. 150° C.

ANALYSIS: Calculated for $C_{16}H_{22}N_4O_4$: 57.47% C 6.63% H 16.76% N Found: 56.97% C 6.36% H 16.67% N

EXAMPLE 22

6-Methoxymethoxy-N-[2-(4-thiomorpholinyl)ethyl]-1,2-benzisoxazol-3-amine a. 3-Amino-6-(methoxymethoxy)-1,2-benzisoxazole To a stirred solution of acetohydroxamic acid (3.88 g) in N,N-dimethylformamide (DMF) (120 ml) was added potassium tertiarybutoxide (tBuOK) (5.80 g) under $N_2$. After one hour of stirring 2-fluoro-4-(methoxymethoxy)-benzonitrile (6.0 g) was added. Stirring continued for 16 hours. TLC (silica gel) in 10% acetone/$CHCl_3$ showed the presence of starting material. An additional 1 equivalent of acetohydroxamic acid and tBuOk were added in DMF (120 ml). After one hour the reaction was diluted with EtOAc (2 l), filtered, washed filtrate with brine (4×11), dried ($MgSO_4$), and concentrated in vacuo. Flash column chromatography (silica gel) was performed eluting with 2.5% acetone/$CH_2Cl_2$ solution affording 8.1 g of the product, m.p. 88–89° C.

ANALYSIS: Calculated for $C_9H_{10}N_2O_3$: 55.67% C 5.19% H 14.32% N Found: 55.73% C 4.80% H 14.29% N b. 6-Methoxymethoxy-N-[2-(4-thiomorpholinyl)ethyl]-1,2-benzisoxazol-3-amine To a solution of 3-amino-6-methoxymethoxy-1,2-benzisoxazole (4.0 g) in N,N-dimethylformamide (DMF) (50 ml) was added sodium hydride (0.74 g) under nitrogen. The reaction was stirred one hour at ambient temperature. A solution of 4-(2-chloroethyl)thiomorpholine (3.6 g) in DMF (25 ml) was added to the reaction and heated to 125° C. for three hours. TLC (5% MeOH/$CH_2Cl_2$) revealed the absence of starting material. The reaction was diluted with EtOAc (1 l), washed with brine (4×500 ml), dried ($MgSO_4$), and concentrated in vacuo. Flash column chromatography (silica gel) eluting with 5% acetone/$CH_2Cl_2$ afforded the the product (2.0 g).

ANALYSIS: Calculated for $C_{15}H_{21}N_3O_3S$: 55.71% C 6.54% H 12.99% N Found: 55.21% C 6.65% H 12.58% N

EXAMPLE 25

5-Methoxy-N-[2-(4-morpholinyl)ethyl]-1,2-benzisoxazol-3-amine a. 5-Methoxy-2-[[(1-methylethylidene)amino]oxy]benzonitrile In 400 ml of DMF was dissolved acetone oxime (34.5 g) followed by potassium t-butoxide (51 g). After this mixture had stirred for 30 minutes, 5-methoxy-2-nitro-benzonitrile (70 g) was added. After stirring overnight, the reaction was diluted with ether (~4 L) and filtered. The filtrate was washed with ethyl acetate and combined organics were washed with water (3×1.5 L), dried ($MgSO_4$) and concentrated in vacuo. Preparative liquid chromatography (silica gel) eluting with 4:1 heptane/EtOAc yielded the expected product (10 g).

b. 3-Amino-5-methoxy-1,2-benzisoxazole

In 125 ml of dry methanol was dissolved 5-methoxy-2-[[(1-methylethylidene)amino]oxy]benzonitrile (10 g), followed by 125 ml of ethereal hydrochloric acid. The reaction was stirred under nitrogen overnight. The reaction was neutralized with saturated sodium carbonate solution and extracted with EtOAc. The organic layer was dried and concentrated in vacuo. Recrystallization of the residue from dichloromethane/petroleum ether afforded the expected product (6.8 g).

c. 5-Methoxy-N-[2-(4-morpholinyl]-1,2-benzosoxazol-3-amine

5-Methoxy-N-[2-(4-morpholinyl)ethyl]-1,2-benzisoxazole-3-amine was prepared from the product of Example 25b following substantially the procedure of Example 8b.

EXAMPLE 26

3-[[(Methylamino)carbonyl][2-(4-morpholinyl)ethyl]amino]-1,2-benzisoxazole-6-yl methylcarbamate To a stirred solution of 3-[[2-(4-morpholinyl)ethyl]amino]-1,2-benzisoxazole-6-ol (Example 9) (1.77 g) and a catalytic amount of copper(I)chloride (0.05 g) in EtOAc (150 ml) was added methyl isocyanate (0.46 g). After 24 hours TLC (silica gel, 1:1:20 acetone/MeOH/DCM) showed no starting material. The reaction was filtered through neutral alumina eluting with 10% MeOH/EtOAc (2 l) and the filtrate was concentrated in vacuo. The residue was further purified by flash chromatography (silica gel) eluting 1:1:20 acetone/MeOH/DCM. The resulting solid was recrystallized from EtOAc/pet. ether to afford 0.5 g of the product, m.p. 138–139° C.

ANALYSIS: Calculated for $C_{17}H_{23}N_5O_5$: 54.10% C 6.14% H 18.56% N Found: 54.08% C 6.34% H 18.61% N

EXAMPLE 27

3-[[(Methylamino)carbonyl][2-(4-morpholinyl)ethyl]amino]-1,2-benzisoxazol-5-yl methylcarbamate To a stirred solution of 3-[[2-(4-morpholinyl)ethyl]amino-1,2-benzisoxazol-5-ol (Example 10) (1 g) and a catalytic amount of copper(I)chloride (0.05 g) in EtOAc (100 ml) was added methyl isocyanate (0.26 g). After 24 hours TLC (silica get, 1:1:20 acetone/MeOH/DCM) showed no starting material. The reaction as filtered through neutral alumina eluting with EtOAc (2 l) and the filtrate was concentrated in vacuo. The residue was further purified by flash chromatography (silica gel) eluting with 1:1:20 acetone/MeOH/DCM. The resulting solid was recrystallized from EtOAc/pet. ether to afford 0.6 g of the product, m.p. 141–142° C.

ANALYSIS: Calculated for $C_{17}H_{23}N_5O_5$: 54.10% C 6.14% H 18.56% N Found: 54.31% C 6.26% H 18.66% N

EXAMPLE 28

7-Bromo-6-methoxy-N-methyl-N-[2-(4-morpholinyl)ethyl]1,2-benzisoxazol-3-amine a. 7-Bromo-3-chloro-6-methoxy-1,2-benzisoxazole To a stirred solution of 3-chloro-6-methoxy-1,2-benzisoxazole (25 g) in acetic acid (200 ml) was added to a solution of bromine (32.6 g) in acetic acid (100 ml) dropwise under $N_2$ at ambient temperature. The mixture was allowed to stir overnight. TLC (silica gel, 5% acetone/$CCl_4$) revealed the presence of starting material. Additional bromine (11 g) in acetic acid (50 ml) was added, and the reaction mixture was allowed to stir overnight. The reaction was filtered and washed with water. The precipitate was collected and recrystallized from methanol to yield the desired compound, m.p. 134–135° C.

ANALYSIS: Calculated for $C_8H_5NO_2BrCl$: 36.61% C 1.92% H 5.34% N Found: 36.49% C 1.87% H 5.40% N b. 7-Bromo-6-methoxy-N-methyl-N-[2-(4-morpholinyl)ethyl]-1,2-benzisoxazol-3-amine 7-Bromo-6-methoxy-N-methyl-N-[2-(4-morpholinyl)ethyl]-1,2-benzisoxazol-3-amine is obtained from the compound of Example 28a following substantially the procedure of Example 1.

EXAMPLE 29

5-Bromo-6-methoxy-N-[2-(4-morpholinyl)ethyl]-1,2-benzisoxazol-3-amine a. 3-Amino-5-bromo-6-methoxy-1,2-benzisoxazole To a stirred solution of 3-amino-6-methoxy-1,2-benzisoxazole (14 g) in methanol (1 L) was added a solution of bromine (13.6 g) and methanol (200 ml) dropwise at −50° C. under $N_2$. The mixture was allowed to warm to room temperature after the addition was complete. After 24 hours an additional ¼ equivalent of bromine was added. TLC (10% acetone/$CHCl_3$) showed no starting material 24 hours later. The reaction was neutralized with saturated $K_2CO_3$ solution, treated with saturated $Na_2SO_3$ solution triturated with water, filtered, and washed with water. The crude product was dried in vacuo affording 14 g of product, m.p. 226–227° C.

ANALYSIS: Calculated for $C_8H_7N_2O_2Br$: 39.53% C 2.90% H 11.53% N Found: 39.93% C 2.59% H 11.42% N b. 5-Bromo-6-methoxy-N-[2-(4-morpholinyl)ethyl]-1,2-benzisoxazol-3-amine 5-Bromo-6-methoxy-N-[2-(4-morpholinyl)ethyl]1,2-benzisoxazol-3-amine is prepared from the compound of Example 29(a) following substantially the procedure used in Example 8(b).

EXAMPLE 30

3-[[2-(4-Thiomorpholinyl)ethyl]amino]-1,2-benzisoxazol-6-ol

6-Methoxymethoxy-N-[2-(4-thiomorpholinyl)ethyl]-1,2-benzisoxazol-3-amine (1.6 g Example 22) was dissolved in methanolic hydrochloric acid (40 ml) and stirred under nitrogen for 24 hours. The reaction was neutralized with saturated $Na_2CO_3$ solution, and extracted with EtOAc. The organic phase was dried over $MgSO_4$ and concentrated in vacuo. The resulting residue was filtered through a silica gel filter-cake eluting with 5% MeOH/DCM, concentrated in vacuo, and subsequent titration with EtOAc provided the product (1.0 g).

ANALYSIS: Calculated for $C_{13}H_{17}N_3O_2S$: 55.89% C 6.13% H 15.04% N Found: 55.68% C 5.89% H 14.61% N

EXAMPLE 31

6-Methoxy-N-methyl-N-[2-[4-(1-phenylmethyl) piperdinyl]ethyl]-1,2-benzisoxazol-3-amine sesquihydrochloride To a sealed tube was added 3-chloro-6-methoxy-1,2-benzisoxazole (1.0 g) and 4-(2-methylaminoethyl)-1-phenylmethylpiperdine (5.0 g). The reaction was heated to 140° C. over 72 hours and then cooled to room temperature. The residue was partitioned between EtOAc and brine, washed with brine (4×), and the organic phase was dried over $MgSO_4$ and concentrated in vacuo. Flash column chromatography (silica gel) eluting with 5% acetone/$CH_2Cl_2$ provided a residue upon evaporization (0.6 g) which was dissolved in ether and made acidic with ethereal hydrochloric acid. The precipitate was dried in vacuo to yield 1.2 g of the expected product.

ANALYSIS: Calculated for $C_{23}H_{29}N_3O_2 \cdot 3/2$ HCl: 63.62% C 7.08% H 9.68% H Found: 63.40% C 6.84% H 9.44% N

EXAMPLE 32

7-Bromo-3-[N-methyl, N-2-(4-morpholinyl)ethyl] amino-1,2-benzisoxazol-6-ol

A stirred solution of 7-bromo-6-methoxy-N-methyl-N-[2-(morpholinyl)ethyl]-1,2-benzisoxazol-3-amine (4.0 g), and lithium bromide (4.7 g) in N,N-dimethylformamide (DMF) (100 ml) was heated to reflux under $N_2$ for 3 hours. The reaction was diluted with EtOAc (11), filtered, washed with brine (4×), dried over $MgSO_4$, and concentrated in vacuo. Flash column chromatography (silica gel) eluting with 1:1:40 acetone/MeOH/$CH_2Cl_2$ afforded 1 g of material. The melting point was 186–187° C.

EXAMPLE 33

7-Bromo-3-[N-methyl, N-2-(4-morpholinyl)ethyl] amino-1,2-benzisoxazol-6-yl dimethylcarbamate To a stirred solution of 7-bromo-3-[N-methyl, N-2-(4-morpholinyl)ethyl]amino-1,2-benzisoxazol-6-ol (0.7 g) and 1,8 diazabicyclo[5.4.0]undec-7-ene (0.09 g) in 1,2-dichloroethane (30 ml) was added dimethylcarbamyl chloride (0.25 g). The mixture was refluxed for 24 hours under $N_2$. TLC (silica gel, 10% MeOH/DCM) showed some starting material. An additional ½ equivalent of dimethylcarbamyl chloride was added and refluxed for 24 more hours. The reaction was filtered and the filtrate concentrated in vacuo. Flash chromatography (silica gel) eluting with 5% acetone/5% MeOH/$CH_2Cl_2$ provided a residue which upon crystallization afforded 0.5 g of the expected compound.

ANALYSIS: Calculated for $C_{17}H_{23}N_4O_4Br$: 47.79% C 5.43% H 13.11% N Found: 47.77% C 5.42% H 12.86% N

EXAMPLE 34

6-Methoxy-N-methyl-N-[2-(2-pyridyl)ethyl]-1,2-benzisoxazol-3-amine hydrochloride hemihydrate To a sealed tube was added 3-chloro-6-methoxy-1,2-benzisoxazole (2.5 g) and 2-(2-methylaminoethyl)pyridine (11.0 g). The reaction was heated to 140° C. over 72 hours and then cooled to room temperature. The residue was partitioned between EtOAc and brine, washed with brine (4×), and the organic phase was dried over $MgSO_4$ and concentrated in vacuo. Preparative liquid chromatography (silica gel) eluting with 5% acetone/$CH_2Cl_2$ provided a residue upon evaporation (1.5 g) which was dissolved in ether and made acidic with ethereal hydrochloric acid. The precipitate was dried in vacuo and recrystallized from ethanol to yield 0.9 g, m.p. 152–153° C.

ANALYSIS: Calculated for $C_{16}H_{17}N_3O_2 \cdot HCl \cdot ½H_2O$: 61.84% C 7.26% H 14.42% N Found: 61.75% C 6.98% H 14.46% N Examples 35–41 are prepared starting with the compound of Example 34 following substantially the procedures set forth in Examples 2–5 and 18.

Examples 42–48 are prepared from Example 31 following substantially the procedures set forth in Examples 2–5 and 18.

EXAMPLE 49

6-Methoxy-N-methyl-N-[2-[1-(4-phenylmethyl) piperazinyl]ethyl]-1,2-benzisoxazol-3-amine Difumarate To a sealed tube was added 3-chloro-6-methoxy-1,2-benzisoxazole (1.32 g) and 1-(2-methylaminoethyl)-4-phenylmethylpiperazine (6.7 g). The reaction was heated to 140° C. over 24 hours and then cooled to room temperature. The residue was partitioned between EtOAc and brine, washed with brine (4×) and the organic phase was dried over $MgSO_4$ and concentrated in vacuo. Flash column chromatography (silica gel) eluting with 2.5% MeOH/EtOAc provided a residue upon evaporation (0.8 g) which was dissolved in ether and made acidic with ethereal fumaric acid. The precipitate was dried in vacuo to yield 1.0 g, m.p. 215–216° C.

ANALYSIS: Calculated for $C_{22}H_{28}N_4O_2 \cdot 2C_4H_4O_4$: 58.82% C 5.92% H 9.15% N Found: 59.26% C 5.78% H 9.43% N Examples 50–56 are prepared starting from the compound of Example 49 and following substantially the procedure set forth in Examples 2–5 and 18.

EXAMPLE 57

6-Methoxy-N-[2-(methylamino)ethyl)-1,2-benzisoxazol-3-amine

To a sealed tube was added 3-chloro-6-methoxy-1,2-benzisoxazole (2.0 g) and N-methylethylenediamine (4.8 g). The reaction was heated to 140° C. over 48 hours and then cooled to room temperature. The residue was partitioned between EtOAc and brine, washed with brine (4×) and the organic phase was dried over $MgSO_4$ and concentrated in vacuo. Flash chromatography (silica gel) eluting with 5% acetone/$CH_2Cl_2$ provided a residue upon evaporation (0.4 g) m.p. 136–137° C.

ANALYSIS: Calculated for $C_{11}H_{15}N_3O_2$: 59.71% C 6.83% H 18.99% N Found: 59.52% C 6.68% H 18.54% N Examples 58–64 are prepared starting from the compound of Example 57 following substantially the procedure set forth in Examples 2–5 and 18.

EXAMPLE 65

6-Methoxy-3-(1-piperazinyl)-1,2-benzisoxazole hemihydrate

To a sealed tube was added 3-chloro-6-methoxy-1,2-benzisoxazole (3.0 g) and piperazine (6.0 g). The reaction was heated to 140° C. over 4 hours and then cooled to room temperature. The residue was dissolved in MeOH and further diluted with EtOAc (11). The precipitate was filtered and the filtrate dried over $MgSO_4$ and concentrated in vacuo. Flash chromatography (silica gel) eluting with 30% MeOH/EtOAc provided a residue upon evaporation (3.6 g), m.p. 79–80° C.

ANALYSIS: Calculated for $C_{12}H_{15}N_3O_2 \cdot \frac{1}{2}H_2O$: 59.49% C 6.65% H 17.34% N Found: 59.25% C 6.28% H 17.30% N Examples 66 to 72 are prepared from the compound of Example 65 following substantially the procedures set forth in Examples 2–5 and 18.

EXAMPLE 73

6-Methoxy-3-[1-(4-aminomethyl)piperidyl]-1,2-benzisoxazole

To a sealed tube was added 3-chloro-6-methoxy-1,2-benzisoxazole (2.0 g) and 4-aminomethylpiperidine (6.2 g). The reaction heated to 140° C. for 24 hours and monitored by TLC (silica gel) (30% MeOH/EtOAc) was complete. The reaction was diluted in MeOH and concentrated in vacuo. The resulting residue was flash chromatographed (silica gel) eluting with 30% MeOH/EtOAc affording a white solid after evaporation. The solid was recrystallized from 15% MeOH/EtOAc/pet. ether to yield 1.0 g. m.p. 89–90° C.

ANALYSIS: Calculated for $C_{28}H_{31}N_3O_2$: 64.35% C 7.33% H 16.08% N Found: 64.26% C 7.49% H 16.20% N Examples 74–80 are prepared starting from the compound of Example 73 and following substantially the procedure set forth in Examples 2–5 and 18.

EXAMPLE 81

6-Methoxy-3-[1-[4-(N,N-diphenylmethyl)aminomethyl]piperidyl]-1,2-benzisoxazole

To a stirred solution of 6-methoxy-3-[1-(4-aminomethyl)piperidyl]-1,2-benzisoxazole (1.0 g), triethylamine (0.8 g) in $CH_2Cl_2$ (30 ml) was added α-bromotoluene (1.3 g) under $N_2$. The reaction was monitored after 24 hours by TLC (silica) (10% MeOH/$CH_2Cl_2$) and was complete. The reaction was diluted with $CH_2Cl_2$ (30 ml), washed with water and brine, dried over $MgSO_4$, and concentrated in vacuo. Flash column chromatography (silica gel) eluting with 5% MeOH/EtOAc provided a solid upon evaporation which was recrystallized from $CH_2Cl_2$/pet. ether to yield 0.25 g, m.p. 107–108° C.

ANALYSIS: Calculated for $C_{28}H_{31}N_3O_2$: 76.16% C 7.08% H 9.52% N Found: 76.23% C 7.40% H 9.66% N Examples 82–88 are prepared starting from the compound of Example 81 and following substantially the procedure set forth in Examples 2–5 and 18.

EXAMPLE 89

6-Methoxy-3-[1-[4-(2-propynyl)]piperazinyl]-1,2-benzisoxazole

To a stirred solution of 6-methoxy-3-(1-piperazinyl)-1,2-benzisoxazole (1.32 g), triethylamine (0.63 g) in $CH_2Cl_2$ (75 ml) was added 3-bromopropyne (1.42 g) under $N_2$. After 24 hours the reaction monitored by TLC (silica gel) (5% MeOH/EtOAc) was complete. The reaction was washed with brine, and water, dried over $MgSO_4$ and concentrated in vacuo. The resulting residue was flash chromatographed (silica gel) eluting with 2.5% MeOH/EtOAc affording a white solid after evaporation. The solid was recrystallized from $CH_2Cl_2$/pet. ether. The product (0.4 g) m.p. 114–115° C.

ANALYSIS: Calculated for $C_{15}H_{17}N_3O_2$: 66.40% C 6.32% H 15.49% N Found: 66.03% C 6.02% H 15.45% N Examples 90–96 are prepared starting from the compound of Example 89 and following substantially the procedure set forth in Examples 2–5 and 18.

EXAMPLE 97

6-Methoxy-3-[1-(N-phenyl)piperazinyl]-1,2-benzisoxazole

A sealed tube was charged with 3-chloro-6-methoxy-1,2-benzisoxazole (0.75 g, 4.1 mmol) and N-phenylpiperazine (2.65 g, 16 mmol) and heated to 140° C. overnight. The reaction was cooled to room temperature, diluted with methanol, and concentrated in vacuo. The material was flash chromatographed (silica gel) eluting with 2:1 $CH_2Cl_2$/heptane to yield a white solid 0.40 g, m.p.=120–121° C., white solid.

ANALYSIS: Calculated for $C_{18}H_{19}N_3O_2$: 69.88% C 6.19% H 13.58% N Found: 69.67% C 6.15% H 13.61% N Examples 98–104 are prepared starting from the compound of Example 97 and following substantially the procedure set forth in Examples 2–5 and 18.

EXAMPLE 105

6-Methoxy-3-[1-(4-pyridyl)piperazinyl)]-1,2-benzisoxazole

To a stirred solution of 6-methoxy-3-(1-piperazinyl)-1,2-benzisoxazole (1.0 g) in DMF (30 ml) was added 4-chloropyridine hydrochloride (0.96 g) under $N_2$ at 120° C. After 4 hours the reaction monitored by TLC (silica gel) (30% MeOH/EtOAc) was complete. The reaction was concentrated in vacuo. The resulting residue was flash chromatographed (silica gel) eluting with 10% MeOH/$CH_2Cl_2$ affording a white solid after evaporation. The solid was recrystallized from 15% MeOH/EtOAc/heptane to yield 0.3 g, m.p. 154–155° C.

ANALYSIS: Calculated for $C_{17}H_{18}N_4O_2$: 65.79% C 5.85% H 18.05% N Found: 65.84% C 5.33% H 17.95% N

EXAMPLE 106

3-[1-(4-Pyridyl)piperazinyl]-1,2-benzisoxazol-6-ol

A stirred solution of 6-methoxy-3-[1-(4-pyridyl)piperazinyl]-1,2-benzisoxazole (1.75 g) and sodium ethylthiolate (0.79 g) in DMF (30 ml) was heated to 105–107° C. under $N_2$ and 3 hours. TLC (silica gel 30% MeOH/$CH_2Cl_2$) showed no presence of starting material. Glacial acetic acid (5 ml) was added and the solvent was removed in vacuo. The residue was flash chromatographed (silica gel) eluting with 10% MeOH/$CH_2Cl_2$ to afford 1.1 g of material. The material was further purified through recrystallization from pyridine to afford 1.0 g of the product, m.p.>250° C.

ANALYSIS: Calculated for $C_{16}H_{16}N_4O_2$: 64.85% C 5.44% H 18.91% N Found: 64.84% C 5.42% H 18.67% N

EXAMPLE 108

3-[1-(4-Pyridyl)piperazinyl]-1,2-benzisoxazol-6-yl dimethylcarbamate

To a stirred solution of 3-[1-(4-pyridyl)piperazinyl]-1,2-benzisoxazol-6-ol (0.80 g) in pyridine (10 ml) was added dimethylcarbamyl chloride (0.70 g) under $N_2$. The reaction was heated to 85° C. for 2 hours. TLC (silica gel 30% $MeOH/CH_2Cl_2$) showed no starting material was present. The solvent was removed in vacuo and the residue was flash chromatographed (silica gel) eluting with 7% MeOH/$CH_2Cl_2$ to afford 0.80 g of material. The material was further purified through recrystallization from $CH_2Cl_2$/pet. ether to afford 0.70 g of the product, m.p. 171–172° C.

ANALYSIS: Calculated for $C_{19}H_{21}N_5O_3$: 62.11% C 5.76% H 19.06% N Found: 61.91% C 5.83% H 18.76% N Examples 107 and 109–112 are prepared starting from the compound of Example 106 and following substantially the procedure set forth in Example 2–5 and 18.

EXAMPLE 113

6-Methoxy-3-[1-(2-pyridyl)piperazinyl]-1,2-benzisoxazole

A sealed tube was charged with 3-chloro-6-methoxy-1,2-benzisoxazole (0.25 g, 1.4 mmol) and 1-(2-pyridyl) piperazine (0.67 g, 4 mmol) and heated to 140° C. overnight. The reaction was cooled to room temperature, diluted with methanol, and concentrated in vacuo. The material was flash chromatographed (silica gel) eluting with $CH_2Cl_2$. The material was further purified through recrystallization from 1,2-dichloroethane/pet. ether to afford 0.15 g of the product, m.p.=123–124° C.

ANALYSIS: Calculated for $C_{17}H_{18}N_4O_2$: 65.79% C 5.85% H 18.05% N Found: 65.43% C 5.56% H 17.67% N Examples 114–120 are prepared starting from the compound of Example 113 and following substantially the procedure set forth in Examples 2–5 and 18.

EXAMPLE 121

3-[1-(4-(6-Chloropyrimidyl))piperazinyl]-6-methoxy-1,2-benzisoxazole

A stirred solution of 6-methoxy-3-(1-piperazinyl)-1,2-benzisoxazole (1.0 g), 4,6-dichloropyrimidine (0.64 g) and sodium bicarbonate (1.08 g) were refluxed in absolute ethanol under $N_2$ for 90 minutes. TLC (silica gel 2/1 acetone/heptane) showed no presence of starting material. The reaction was allowed to cool to room temperature, partitioned between $CH_2Cl_2$ and water, extracted with $CH_2Cl_2$, dried over $MgSO_4$ and concentrated in vacuo to afford 1.44 g of material. The material was further purified through recrystallization from $CH_2Cl_2$/pet. ether to yield the product 1.1 g, m.p. 203–204° C.

ANALYSIS: Calculated for $C_{16}H_{16}N_5O_2Cl$: 55.58% C 4.66% H 20.25% N Found: 55.57% C 4.66% H 20.02% N Examples 122–128 are prepared starting from the compound of Example 121 and following substantially the procedure set forth in Examples 2–5 and 18.

EXAMPLE 129

3-[1-(2-(6-Chloro)pyrazinyl]-6-methoxy-1,2-benzisoxazole

A stirred solution of 6-methoxy-3-(1-piperazinyl)-1,2-benzisoxazole (1.0 g, 4.3 mmol) in DMF (10 ml) was added 2,6-dichloropyrazine (0.95 g, 6.4 mmol) under $N_2$. The reaction was heated to 140° C. for 4 hours and concentrated in vacuo. The material was filtered, washing with $CH_2Cl_2$, washings were collected, and concentrated in vacuo. The residue was flash chromatographed (silica gel) eluting with 5% acetone/$CH_2Cl_2$ to yield a white solid 0.50 g, m.p. 175–176° C.

ANALYSIS: Calculated for $C_{16}H_{16}N_5O_2Cl$: 55.58% C 4.66% H 20.25% N Found: 55.41% C 4.60% H 20.18% N Examples 130–136 are prepared starting from the compound of Example 129 and following substantially the procedure set forth in Examples 2–5 and 18.

EXAMPLE 137

3-[1-(3-(6-Chloro)pyridazinyl)piperzinyl]-6-methoxy-1,2-benzisoxazole

To a stirred solution of 6-methoxy-3-(1-piperazinyl)-1,2-benzisoxazole (1.0 g, 4.3 mmol) in DMF (10 ml) was added 3,6-dichloropyridazine (0.95 g, 6.4 mmol) under $N_2$. The reaction was heated to 140° C. overnight. The reaction was allowed to cool to room temperature and concentrated in vacuo. The material was recrystallized from ethanol to afford 0.70 g, m.p.=237–238° C.

ANALYSIS: Calculated for $C_{16}H_{16}N_5O_2Cl$: 55.58% C 4.66% H 20.25% N Found: 55.72% C 4.29% H 20.17% N Examples 138–144 are prepared starting from the compound of Example 137 and following substantially the procedure set forth in Examples 2–5 and 18.

EXAMPLE 145

6-Methoxy-3-[1-(4-phenylmethyl)piperazinyl]-1,2-benzisoxazole

To a sealed tube was added 3-chloro-6-methoxy-1,2-benzisoxazole (2.0 g) and N-phenylmethylpiperazine (7.7 g). The reaction was heated to 140° C. for 24 hours and monitored by TLC (silica gel) (5% MeOH/EtOAc) was complete. The reaction was diluted in MeOH and EtOAc (1:4), washed with brine, dried over $MgSO_4$ and concentrated in vacuo. The resulting residue was flash chromatographed (silica gel) eluting with 5% $MeOH/CH_2Cl_2$ affording a white solid after evaporation. The solid was recrystallized from $CH_2Cl_2$/pet. ether to yield 2.5 g, m.p. 99–100° C.

ANALYSIS: Calculated for $C_{19}H_{21}N_3O_2$: 70.57% C 6.55% H 12.99% N Found: 70.41% C 6.54% H 13.04% N Examples 146–152 are prepared starting from the compound of Example 145 and following substantially the procedure set forth in Examples 2–5 and 18.

EXAMPLE 153

6-Methoxy-3-[1-[4-(3-methyl)phenylmethyl] piperazinyl]-1,2-benzisoxazole

To a sealed tube was added 6-methoxy-3-(1-piperazinyl)-1,2-benzisoxazole (1.04 g), triethylamine (0.68 g) in $CH_2Cl_2$ (100 ml) was added α-bromo-m-xylene (0.91 g) under $N_2$. After 24 hours the reaction monitored by TLC (silica gel) was complete. The reaction was washed with water and brine, dried over $MgSO_4$, and concentrated in vacuo. The resulting residue was flash chromatographed (silica gel) eluting with 10% acetone/$CH_2Cl_2$ affording a white solid after evaporation. The solid was recrystallized from $CH_2Cl_2$/pet. ether to yield 0.3 g, m.p. 106–106° C.

ANALYSIS: Calculated for $C_{20}H_{23}N_3O_2$: 71.19% C 6.87% H 12.45% N Found: 71.11% C 6.75% H 12.39% N Examples 154–160 are prepared starting from the compound of Example 153 and following substantially the procedure set forth in Examples 2–5 and 18.

EXAMPLE 161

6-Methoxy-3-[1-(4-quinolinyl)piperazinyl]-1,2-benzisoxazole hydrochloride

To a stirred solution of 6-methoxy-3-(1-piperazinyl)-1,2-benzisoxazole (1.0 g) in DMF (10 ml) was added 4-chloroquinoline (1.05 g) uner $N_2$. The reaction was heated to 140° C. for 2 hours and concentrated in vacuo. The material was filtered washing with $CH_2Cl_2$. The material was further purified through recrystallization from MeOH to yield 0.85 g, m.p. 266–267° C.

ANALYSIS: Calculated for $C_{21}H_{20}N_4O_2 \cdot HCl$: 63.55% C 5.33% H 14.12% N Found: 63.54% C 5.17% H 13.98% N Examples 162–168 are prepared starting from the compound of Example 161 and following substantially the procedure set forth in Examples 2–5 and 18.

EXAMPLE 169

6-Methoxy-3-[1-(4-(7-trifluoromethyl)quinolinyl) piperazinyl]-1,2-benzisoxazole hydrochloride hemihydrate To a stirred solution of 6-methoxy-3-(1-piperazinyl)-1,2-benzisoxazole (0.50 g, 2.1 mmol) in DMF (10 ml) was added 4-chloro-7-trifluoromethylquinoline (0.75 g, 3.2 mmol) under $N_2$. The reaction was heated to 140° C. for 2 hours and concentrated in vacuo. The material was filtered washing with $CH_2Cl_2$. The material was further purified through recrystallization from MeOH to yield 0.40 g, m.p.= >250° C.

ANALYSIS: Calculated for $C_{22}H_{19}N_4O_2F_3 \cdot HCl \cdot \frac{1}{2}H_2O$: 55.76% C 4.46% H 11.82% N Found: 56.19% C 4.00% H 11.86% N Examples 170–176 are prepared starting from the compound of Example 169 and following substantially the procedure set forth in Examples 2–5 and 18.

EXAMPLE 177

3-[1-(4-(7-Chloro)quinolinyl)piperazinyl]-6-methoxy-1,2-benzisoxazole hydrochloride hemihydrate To a stirred solution of 6-methoxy-3-(1-piperazinyl)-1,2-benzisoxazole (0.50 g, 2.1 mmol) in DMF (10 ml) was added 4,7-dichloroquinoline (0.64 g, 3.2 mmol) under $N_2$. The reaction was heated to 140° C. for 2 hours and concentrated in vacuo. The material was filtered washing with $CH_2Cl_2$. The material was further purified through recrystallization from MeOH to yield 0.40 g, m.p.=210–211° C.

ANALYSIS: Calculated for $C_{21}H_{19}N_4O_2Cl \cdot HCl \cdot \frac{1}{2}H_2O$: 57.28% C 4.81% H 12.72% N Found: 57.69% C 4.65% H 12.57% N Examples 178–184 are prepared starting from the compound of Examples 177 and following substantially the procedure set forth in Examples 2–5 and 18.

EXAMPLE 185

7-Bromo-6-methoxy-3-(1-piperazinyl)-1,2-benzisoxazole hydrochloride

To a sealed tube was added 7-bromo-3-chloro-6-methoxy-1,2-benzisoxazole (2.0 g) and piperazine (2.6 g). The reaction was heated to 140° C. over 30 minutes and then cooled to room temperature. The residue was dissolved in MeOH and concentrated in vacuo. Flash column chromatography (silica gel) eluting with 30% MeOH/EtOAc provided a residue upon evaporation (1.0 g) which was recrystallized from MeOH/$CH_2Cl_2$/pet. ether to yield 1.0 g, m.p. 268–269° C.

ANALYSIS: Calculated for $C_{12}H_{14}N_3O_2Br \cdot HCl$: 41.34% C 4.34% H 12.05% N Found: 40.79% C 4.23% H 11.84% N

EXAMPLE 186

7-Bromo-6-methoxy-3-[1-(4-pyridyl)piperazinyl]-1,2-benzisoxazole

A stirred solution of 7-bromo-6-methoxy-3-piperazinyl-1,2-benzisoxazole hydrochloride (1.40 g) and 4-chloropyridine hydrochloride (1.01 g) in DMF (30 ml) was heated to 120° C. under $N_2$ for 4 hours. TLC (silica gel 30% MeOH/$CH_2Cl_2$) showed no presence of starting material. The solvent was removed in vacuo and the residue was flash chromatographed (silica gel) eluting with 5% MeOH/$CH_2Cl_2$ to afford 0.75 g (43%) of the product, m.p. 183–184° C.

ANALYSIS: Calculated for $C_{17}H_{17}N_4O_2Br$: 52.46% C 4.40% H 14.39% N Found: 52.35% C 4.28% H 14.37% N It should be understood that this specification and examples are set forth by way of illustration and not limitation and that various modifications and changes may be made without departing from the spirit and scope of the present invention as defined by the appended claims.

We claim:

1. A compound of the formula

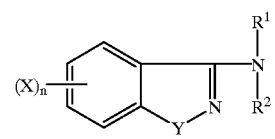

wherein $R^1$ is hydrogen, $(C_1-C_6)$alkyl, aryl$(C_1-C_6)$alkyl, $(C_1-C_6)$ alkoxycarbonyl, aryloxycarbonyl, aryl$(C_1-C_6)$ alkoxycarbonyl, aminocarbonyl, $(C_1-C_6)$ alkylaminocarbonyl, or di$(C_1-C_6)$alkylaminocarbonyl;

X is hydrogen, $(C_1-C_6)$alkyl, $(C_1-C_6)$alkoxy, $(C_1-C_6)$ alkoxymethyleneoxy, aryl$(C_1-C_6)$alkoxy, halo, hydroxy, amino, $(C_1-C_6)$alkylamino, di$(C_1-C_6)$ alkylamino, aryl$(C_1-C_6)$alkylamino, $(C_1-C_6)$ alkanoylamino, aminocarbonyloxy, $(C_1-C_{10})$ alkylaminocarbonyloxy, di$(C_1-C_{10})$ alkylaminocarbonyloxy, tetrahydroisoquinolylcarbonyloxy, aryl$(C_1-C_{10})$ alkylaminocarbonyloxy, $(C_1-C_6)$alkoxycarbonyloxy, aryl$(C_1-C_6)$alkylcarbonyloxy;

Y is oxygen, sulfur or $NR^{10}$ where $R^{10}$ is hydrogen, $(C_1-C_6)$alkyl, aryl or aryl$(C_1-C_6)$alkyl;

$R^2$ is where $R^3$ is hydrogen, $(C_1-C_6)$alkyl, aryl$(C_1-C_6)$alkyl, $(C_1-C_6)$ alkylcarbonyl, $(C_1-C_6)$alkoxycarbonyl, $(C_3-C_6)$ alkenyl, $(C_3-C_6)$alkynyl, aryl, amino$(C_1-C_6)$alkyl, mono$(C_1-C_6)$alkylamino$(C_1-C_6)$alkyl or di$(C_1-C_6)$ alkylamino$(C_1-C_6)$alkyl;

$R^4$ is hydrogen or $(C_1-C_6)$alkyl;

m is an integer from 2 to 7;

n is 0 or an integer of 1 to 3 with the proviso that when Y is S, $R^1$ is not hydrogen or $(C_1-C_6)$alkyl and when Y is $NR^{10}$, $R^3$ is not hydrogen, $(C_1-C_6)$alkyl, aryl$(C_1-C_6)$alkyl or aryl;

and pharmaceutically acceptable addition salts thereof and optical and geometric isomers or racemic mixtures thereof.

2. The compound of claim 1 of the formula

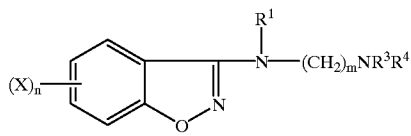

wherein

X is hydrogen, $(C_1-C_6)$alkyl, $(C_1-C_6)$alkoxy, $(C_1-C_6)$alkoxymethyleneoxy, aryl$(C_1-C_6)$alkoxy, halo, hydroxy, $(C_1-C_6)$alkanoylamino, aminocarbonyloxy, $(C_1-C_{10})$alkylaminocarbonyloxy, di$(C_1-C_{10})$alkylaminocarbonyloxy, aryl$(C_1-C_{10})$alkylaminocarbonyloxy, $(C_1-C_6)$alkoxycarbonyloxy, tetrahydroisoquinolylcarbonyloxy or aryl$(C_1-C_6)$alkylcarbonyloxy;

$R^1$ is hydrogen, $(C_1-C_6)$alkyl, aryl$(C_1-C_6)$alkyl, $(C_1-C_6)$alkoxycarbonyl, aryloxycarbonyl, aryl$(C_1-C_6)$alkoxycarbonyl, aminocarbonyl, $(C_1-C_6)$alkylaminocarbonyl, or di$(C_1-C_6)$alkylaminocarbonyl;

$R^3$ is hydrogen, $(C_1-C_6)$alkyl, aryl$(C_1-C_6)$alkyl, $(C_1-C_6)$alkylcarbonyl, $(C_1-C_6)$alkoxycarbonyl, $(C_3-C_6)$alkenyl, $(C_3-C_6)$alkynoyl, aryl, amino$(C_1-C_6)$alkyl, mono$(C_1-C_6)$alkylamino, $(C_1-C_6)$alkyl or di$(C_1-C_6)$alkylamino$(C_1-C_6)$alkyl;

$R^4$ is hydrogen or $(C_1-C_6)$alkyl;

m is an integer from 2 to 7;

n is an integer from 0 to 3; and pharmaceutically acceptable acid addition salts thereof and optical and geometric isomers or racemic mixtures thereof.

3. The compound of claim 2 wherein

X is hydrogen, hydroxy, halo, $(C_1-C_6)$alkyl, $(C_1-C_6)$alkoxy, $(C_1-C_8)$alkylaminocarbonyloxy, tetrahydroisoquinolylcarbonyloxy, di$(C_1-C_8)$alkylaminocarbonyloxy or aryl$(C_1-C_6)$alkylaminocarbonyloxy;

$R^1$ is hydrogen or $(C_1-C_6)$alkyl;

$R^3$ is $(C_1-C_6)$alkyl;

$R^4$ is hydrogen n is 1 or 2; and m is 2, 3 or 4.

4. The compound of claim 3 wherein

X is hydrogen, 5-hydroxy, 5-methoxy, 5-methylaminocarbonyloxy, 5-dimethylaminocarbonyloxy, 5-methylethylaminocarbonyloxy, 5-bromo, 7-bromo, 5-phenylmethylaminocarbonyloxy, 6-chloro, 6-hydroxy, 6-methoxy, 6-methylaminocarbonyloxy, 6-methylethylaminocarbonyloxy, 6-dimethylaminocarbonyloxy, 6-phenylmethylaminocarbonyloxy, 5-hexylaminocarbonyloxy, 5-heptylaminocarbonyloxy, 5-tetrahydroisoquinol-2-ylcarbonyloxy, 6-hexylaminocarbonloxy, 6-heptylaminocarbonyloxy or 6-tetrahydroisoquinol-2-ylcarbonyloxy;

$R^1$ is hydrogen or methyl;

$R^3$ is methyl;

$R_4$ is hydrogen; and m is 2.

5. The compound of claim 4 which is 6-methoxy-N-[2-(methylamino)ethyl)-1,2-benzisoxazol-3-amine and its pharmaceutically acceptable acid addition salts.

* * * * *

UNITED STATES PATENT AND TRADEMARK OFFICE
CERTIFICATE OF CORRECTION

PATENT NO.   : 5,925,766
DATED        : July 20, 1999
INVENTOR(S)  : Gerald J. O'Malley and Mark G. Palermo It is certified that error appears in the above-identified patent and that said Letters Patent is hereby corrected as shown below:

Column 2,
Line 7 reads as "($C_1$ 14 $C_6$)" and should read as -- ($C_1$-$C_6$) --.
Line 36 reads as "shall means" and should read as -- shall mean --.

Column 3,
Line 18 reads as "($C_1$-$C_6$)alkoxycarbonyl," and should read as -- ($C_1$-$C_6$)alkylcarbonyl --.
Line 50 reads as "tetrahydroisoquinolylcarbonyloxyl" and should read as
-- tetrahydroisoquinolycaronyloxy--.

Column 5,
Line 52 reads as "dimethylaminocabonyloxy" and should read as
--dimethylaminocarbonyloxy--.

Column 7,
Lines 3 & 4 reads as "($C_1$-$C_{10}$)alkylaminocarbonyloxy," and should read as -- ($C_1$-$C_6$) alkoxycarbonyloxy--.
Line 22 reads as "aminocarbonyloxy" and should read as -- alkylaminocarbonyloxy, --.
Line 36 should include -- 5-hexylaminocarbonyloxy, 5-heptylaminocarbonyloxy, --.

Column 8,
Lines 50 & 51 reads as "($C_1$-$C_6$)alkenyl, ($C_3$-$C_6$)alkynyl," and should read as
-- ($C_1$-$C_6$)alkyl, ($C_2$-$C_6$)alkenyl, ($C_3$-$C_6$)alkynyl, --.

Column 11,
Line 66 reads as "6-haptylaminocarbonyloxy" and should read
as --6-heptylaminocarbonyloxy--.

Column 17,
Line 7 reads as "meaning" and should read as -- meanings --.

Column 21,
Line 14 should include the Structure caption -- (XV) --.
Line 26 reads as "temperature," and should read as -- temperatures, --.

UNITED STATES PATENT AND TRADEMARK OFFICE
CERTIFICATE OF CORRECTION

PATENT NO.   : 5,925,766
DATED        : July 20, 1999
INVENTOR(S)  : Gerald J. O'Malley and Mark G. Palermo It is certified that error appears in the above-identified patent and that said Letters Patent is hereby corrected as shown below:

Column 24,
Line 51 reads "obtained form" and should read as -- obtained from --.

Column 37,
Ex No 48 reads as "CH" and should read as -- $CH_3$ --.

Column 67,
Line 40 reads as "and concentration" and should read as -- and concentrated --.

Column 70,
Line 18 reads as "amine]" and should read as -- amino] --.
Line 34 reads as "-3amine" and should read as -- -3-amine --.

Column 71,
Line 15 reads as "59.30%" and should read as -- 59.30%C --.

Column 73,
Line 2 reads as "the the" and should read as -- the --.

Column 74,
Line 1 reads as "as filtered" and should read as -- was filtered --.
Line 17 reads as "(200 ml) was added to a" and should read as -- (200 ml) was added a --.

Column 78,
Line 52 reads as "$N_2$ and 3 hours" and should read as -- $N_2$ for 3 hours. --.

Column 79,
Line 56 reads as "pyrazinyl]-6-"and should read as -- pyrazinyl)piperazinyl] --.

Column 81,
Line 1 reads as "uner" and should read as -- under --.

UNITED STATES PATENT AND TRADEMARK OFFICE
CERTIFICATE OF CORRECTION

PATENT NO. : 5,925,766
DATED : July 20, 1999
INVENTOR(S) : Gerald J. O'Malley and Mark G. Palermo It is certified that error appears in the above-identified patent and that said Letters Patent is hereby corrected as shown below:

Column 82,
Line 50 in claim 1, the definition of $R^2$ is missing, which should read as -- $R^2$ is

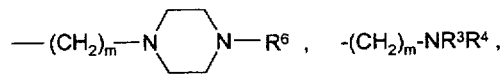

or

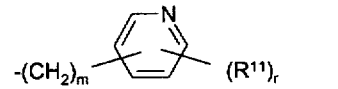

or $R^1$ and $R^2$ together with the nitrogen to which they are attached form the ring

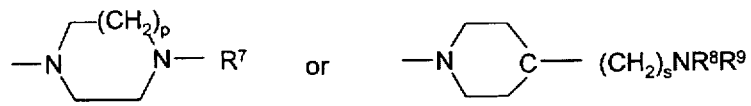

--.

Signed and Sealed this

Thirtieth Day of October, 2001

Attest:

*Nicholas P. Godici*

NICHOLAS P. GODICI
*Attesting Officer*   Acting Director of the United States Patent and Trademark Office

UNITED STATES PATENT AND TRADEMARK OFFICE
CERTIFICATE OF CORRECTION

PATENT NO. : 5,925,766
DATED : July 20, 1999
INVENTOR(S) : Gerald J. O'Malley and Mark G. Palermo It is certified that error appears in the above-identified patent and that said Letters Patent is hereby corrected as shown below:

Column 2,
Line 7, reads as "($C_1$ 14 $C_6$)" and should read as -- ($C_1$-$C_6$) --.
Line 36, reads as "shall means" and should read as -- shall mean --.

Column 3,
Line 18, reads as "($C_1$-$C_6$)alkoxycarbonyl," and should read as -- ($C_1$-$C_6$) alkylcarbonyl --.
Line 50, reads as "tetrahydroisoquinolylca<u>rb</u>onyloxyl" and should read as -- tetrahydroisoquinolylcaronyloxy --.

Column 5,
Line 52, reads as "dimethylaminocabonyloxy" and should read as -- dimethylaminoc<u>ar</u>bonyloxy --.

Column 7,
Lines 3 & 4, reads as "($C_1$-$C_{10}$)alkylaminocarbonyloxy," and should read as -- ($C_1$-$C_6$) alkoxycarbonyloxy --.
Line 22, reads as "aminocarbonyloxy" and should read as -- alkylaminocarbonyloxy, --.
Line 36, should include -- 5-hexylaminocarbonyloxy, 5-heptylaminocarbonyloxy, --.

Column 8,
Lines 50 & 51, reads as "($C_1$-$C_6$)alkenyl, ($C_3$-$C_6$)alkynyl," and should read as -- ($C_1$-$C_6$) alkyl, ($C_2$-$C_6$)alkenyl, ($C_3$-$C_6$)alkynyl, --.

Column 11,
Line 66, reads as "6-haptylaminocarbonyloxy" and should read as -- 6-heptylaminocarbonyloxy --.

Column 17,
Line 7, reads as "meaning" and should read as -- meanings --.

Column 21,
Line 14, should include the Structure caption -- (XV) --.
Line 26, reads as "temperature," and should read as -- temperatures, --.

UNITED STATES PATENT AND TRADEMARK OFFICE
CERTIFICATE OF CORRECTION

PATENT NO. : 5,925,766
DATED : July 20, 1999
INVENTOR(S) : Gerald J. O'Malley and Mark G. Palermo It is certified that error appears in the above-identified patent and that said Letters Patent is hereby corrected as shown below:

Column 24,
Line 51, reads "obtained form" and should read as -- obtained from --.

Column 37,
Ex. No 48, reads as "CH" and should read as -- $CH_3$ --.

Column 67,
Line 40, reads as "and concentration" and should read as -- and concentrated --.

Column 70,
Line 18, reads as "amine]" and should read as -- amino] --.
Line 34, reads as "-3amine" and should read as -- 3-amine --.

Column 71,
Line 15, reads as "59.30%" and should read as -- 59.30%C --.

Column 73,
Line 2, reads as "the the" and should read as -- the --.

Column 74,
Line 1, reads as "as filtered" and should read as -- was filtered --.
Line 17, reads as "(200 ml) was added to a" and should read as -- (200 ml) was added a --.

Column 78,
Line 52, reads as "$N_2$ and 3 hours" and should read as -- $N_2$ for 3 hours. --.

Column 79,
Line 56, reads as "pyrazinyl]-6-"and should read as -- pyrazinyl)piperazinyl] --.

Column 81,
Line 1 reads as "uner" and should read as -- under --.

UNITED STATES PATENT AND TRADEMARK OFFICE
CERTIFICATE OF CORRECTION

PATENT NO. : 5,925,766
DATED : July 20, 1999
INVENTOR(S) : Gerald J. O'Malley and Mark G. Palermo It is certified that error appears in the above-identified patent and that said Letters Patent is hereby corrected as shown below:

Column 82,
Line 50 in claim 1, the definition of $R^2$ is missing, which should read as
-- $R^2$ is

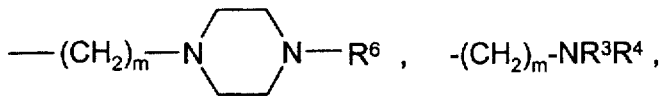

or

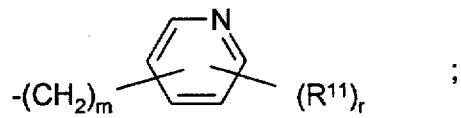

or $R^1$ and $R^2$ together with the nitrogen to which they are attached form the ring

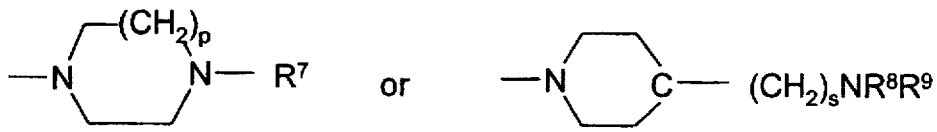

--.

Signed and Sealed this

Eleventh Day of December, 2001

Attest:

NICHOLAS P. GODICI
Attesting Officer   Acting Director of the United States Patent and Trademark Office